(12) United States Patent
Guo et al.

(10) Patent No.: US 8,575,422 B2
(45) Date of Patent: Nov. 5, 2013

(54) *ZEA* MAIZE AUXIN RESPONSE RELATED GENES FOR CONTROLLING PLANT GROWTH AND ORGAN SIZE AND THEIR USE IN IMPROVING CROP PLANTS

(75) Inventors: Mei Guo, West Des Moines, IA (US); Mary A Rupe, Altoona, IA (US); Wesley B Bruce, Raleigh, NC (US); Rajeev Gupta, Johnston, IA (US); Carl R Simmons, Des Moines, IA (US)

(73) Assignee: Pioneer Hi Bred International Inc., Johnston, IA (US)

( * ) Notice: Subject to any disclaimer, the term of this patent is extended or adjusted under 35 U.S.C. 154(b) by 441 days.

(21) Appl. No.: 12/846,017

(22) Filed: Jul. 29, 2010

(65) Prior Publication Data

US 2010/0293670 A1 Nov. 18, 2010

Related U.S. Application Data

(63) Continuation of application No. 12/464,144, filed on May 12, 2009, now Pat. No. 7,834,240, which is a continuation of application No. 11/692,977, filed on Mar. 29, 2007, now Pat. No. 7,550,575.

(60) Provisional application No. 60/788,123, filed on Mar. 31, 2006.

(51) Int. Cl.
*A01H 1/00* (2006.01)
*A01H 5/00* (2006.01)
*C12N 15/82* (2006.01)

(52) U.S. Cl.
USPC ........... 800/278; 800/290; 800/298; 800/306; 800/312; 800/314; 800/320; 800/320.1; 800/320.2; 800/320.3; 800/322; 435/410; 435/419

(58) Field of Classification Search
None
See application file for complete search history.

(56) References Cited

U.S. PATENT DOCUMENTS

| 5,350,836 | A | * | 9/1994 | Kopchick et al. | 530/399 |
|---|---|---|---|---|---|
| 7,569,389 | B2 | | 8/2009 | Feldman et al. | |
| 2004/0214272 | A1 | | 10/2004 | La Rosa et al. | |
| 2004/0216190 | A1 | * | 10/2004 | Kovalic | 800/289 |
| 2009/0019601 | A1 | | 1/2009 | Kovalic | |
| 2010/0083407 | A1 | | 4/2010 | Feldmann et al. | |

OTHER PUBLICATIONS

Okushima, Y., et al.; "Functional Genomic Analysis of the Auxin Response Factor Gene Family Members in *Arabidopsis thaliana*: Unique and Overlapping Functions of ARF7 and ARF19"; The Plant Cell (Feb. 2005) 17:444-463; American Society of Plant Physiologists; Rockville, MD US.

Hay, A., et al.; "PINing down the connections: transcription factors and hormones in leaf morphogenesis"; Current Opinion in Plant Biology (2004) 7:575-581; Elsevier Ltd.; Amsterdam, The Netherlands.

Fleming, A.; "Formation of primordia and phyllotaxy"; Current Opinion in Plant Biology (2005) 8:53-58; Elsevier Ltd.; Amsterdam, The Netherlands.

Teale, W., et al.; "Auxin and the developing root of *Arabidopsis thaliana*"; Physiologia Plantarum (2005) 123:130-138; Munksgaard International Publishers Ltd; Copenhagen, Denmark.

Weiss, J., et al.; "Genetic control of floral size and proportions"; Int J Dev Biol (2005) 49:513-525; UBC Press, Spain.

Hill, M., et al.; "Functional Analysis of Conserved Histidines in ADP-Glucose Pyrophosphorylase from *Escherichia coli*"; Biochemical and Biophysical Research Communications (1998) 244:573-577; Elsevier Inc.; The Netherlands.

Guo, H., et al.; "Protein tolerance to random amino acid change"; PNAS (Jun. 22, 2004) 101(25)9205-9210; National Academy of Sciences; Washington DC, US.

Lazar, E., et al.; "Transforming Growth Factor alpha: Mutation of Aspartic Acid 47 and Leucine 48 Results in Different Biological Activities"; Molecular and Cellular Biology (Mar. 1988) 8(3):1247-1252; American Society for Microbiology; Washington, DC, US.

* cited by examiner

*Primary Examiner* — Eileen B O Hara
(74) *Attorney, Agent, or Firm* — Pioneer Hi-Bred Int'l Inc.

(57) ABSTRACT

The present invention provides polynucleotides and related polypeptides (SEQ ID NO: 11 and 44) of the ZmARGOS (Auxin-Regulated Gene involved in Organ Size) gene family. The invention provides genomic sequence for the ZmARGOS genes. ZmARGOS is responsible for controlling plant growth, organ size and yield in crop plants. Transgenic plants expressing ZmARGOS show a positive impact on biomass accumulation and rate of maize plant growth, as well as an increase in organ size. These maize genes will find utility for enhancing agronomic traits in maize (and other crops).

4 Claims, 6 Drawing Sheets

FIGURE 2A

```
                                      1                                                    50
AtARGOS_1A  SEQ ID NO: 26 (32-147) (1) --------------------------------------MDVG-RNNRKMSFR--
AtARGOS_1B  SEQ ID NO:26         (1) --------------------------MIREISNLQKDIINIQDSYSNNRVMDVG-RNNRKMSFR--
AtARGOS_2   SEQ ID NO:27         (1) --------------------------MIREFSSLQNDIINIQEHYSLNNNMDVRGDHNRKNTSFRGS
AtARGOS_3   SEQ ID NO:28         (1) --------------------------------------------------MRVH
OsARGOS_1   SEQ ID NO:13         (1) --------------------------------MKTLAVVEGTRAHIVNLANSRASRLN
OsARGOS_2   SEQ ID NO:14         (1) ----------------------------------------------------
OsARGOS_3   SEQ ID NO:15         (1) --------------MSFAIRSSEPEFWFLIPSEAAVAVAAHRLVVMDQRRSGSAYRP
OsARGOS_4   SEQ ID NO:16         (1) ------------------------------MEKGR--------GKACGGGSTAPPPPPSS
OsARGOS_5   SEQ ID NO:17         (1) --------------------MRGVILLRYEEDAMAGHRSTAAATGG------RLYGQVGVK
OsARGOS_6   SEQ ID NO:18         (1) ----------------------------------------------------
OsARGOS_7   SEQ ID NO:19         (1) -----------------------------------MEGVGARQRRNPLIPR
OsARGOS_8   SEQ ID NO:20         (1) -----------------------MEEQMFREQQMQRGGRHHQHHTTREQ
ZmARGOS_1   SEQ ID NO:2          (1) ---------------MSTTRPEDTQQLINSAAASPNRSAPSAAPSD
ZmARGOS_2   SEQ ID NO:4          (1) ---------------MSAGPEDTQQLINSAAASPNRSAPSAAPSD
ZmARGOS_3   SEQ ID NO:6          (1) -------------------------------MASRSSAMEGGAAIQRR--
ZmARGOS_4   SEQ ID NO:7          (1) -MCRGLPTPAPAPALQFQSQDCSRQQRGTTQAPPGRASESVRACMAAER
ZmARGOS_5   SEQ ID NO:8          (1) --------------------MHLLDDLRQDRGGAAAHTG-------SRSRKPPPP
ZmARGOS_6   SEQ ID NO:9          (1) ----------------------------------------------------
ZmARGOS_7   SEQ ID NO:10         (1) -----------------------------MPSSSQTPPPVGRT
ZmARGOS_8   SEQ ID NO:11         (1) --------------------------------MMLHCTFAISEAP
ZmARGOS_9   SEQ ID NO:12         (1) -------------MPVASSLMAMELETDQLAWAEQQRQQNRRQTMVV
GmARGOS_1   SEQ ID NO:21         (1) --------------------------------------------MMMVH
GmARGOS_2   SEQ ID NO:22         (1) --------------------------------------------MMMVH
GmARGOS_3   SEQ ID NO:23         (1) ----------------------------------------------------
GmARGOS_4   SEQ ID NO:24         (1) ----------------------------------------------------
GmARGOS_5   SEQ ID NO:25         (1) ----------------------------------------------------
SbARGOS_1   SEQ ID NO:29         (1) ---------------MSTGRPEDIQQLINSATSSPNRTSPSASPSD
SbARGOS_3   SEQ ID NO:30         (1) ----------------------MASRSSALEGGGAAIQRR--
SbARGOS_2   SEQ ID NO:31         (1) ----------------------------------------------------
SbARGOS_4   SEQ ID NO:32         (1) ----------------------------------------------------
SbARGOS_5   SEQ ID NO:33         (1) MSFVAGSSEADQLWFLIPSEQARAHAVQPHHPLAMDRRSSARRGDPHPH
SbARGOS_6   SEQ ID NO:34         (1) ------------------MAEERKQAGSRWPAGG--------SGGGRMRDA
SbARGOS_7   SEQ ID NO:35         (1) ----------------------------------------------------
SbARGOS_8   SEQ ID NO:36         (1) -----------------------------------MPSPSQTSPP-VGRR
SbARGOS_9   SEQ ID NO:37         (1) ----------------------------------------------------

Consensus
```

```
                        51                                                           100
AtARGOS_1A_pep   (15)   -SSPEKSKQELRRSFSAQK------------------------------------------RMMIPAN
AtARGOS_1B_pep   (39)   -SSPEKSKQELRRSFSAQK------------------------------------------RMMIPAN
AtARGOS_2_pep    (42)   APAPIMGKQELFRTLSSQNSP----------------------------------------RRLISAS
AtARGOS_3_pep     (5)   DQRLRFDVTPKPMGLN------------------------------------------------GSS
OsARGOS_1_pep    (28)   ERLIDPAIESRSIAGATPAP--------------------------------------------F
OsARGOS_2_pep     (1)   ----------------------------------------------------------------
OsARGOS_3_pep    (45)   KRTHMAAAEDEHRRPGTSSRRR---------------------------VAPTPTTQTQTAPG
OsARGOS_4_pep    (24)   SGKSGGGGGSNIREAAAS----------------------------------------GGGGVWGK
OsARGOS_5_pep    (36)   RRVVEETAAAVEVGGGGGG------------------------------------------
OsARGOS_6_pep     (1)   ------------------MQEEAASS-------------------------------SSSSASPVM
OsARGOS_7_pep    (17)   PNGSKRHLQH--QHQPNAA------------------------------------------EKKTAATSN
OsARGOS_8_pep    (27)   EQQQKQQQRRRLMNNATNG------------------------------------------GGGDGGSRC
ZmARGOS_1_pep    (32)   MERGSGTAASSSRASTTSHSHQRATHRVEEEEEEPSSSRGG-GSLCSG
ZmARGOS_2_pep    (31)   MERGSGTAASSSRASTTSHSHQRATHRVEEEEEE--PSSSRGA-GSLCSG
ZmARGOS_3_pep    (18)   -NAVKRHLQQ--RQQEADF-----------------------------------------LDKKVIAST
ZmARGOS_4_pep    (49)   KAASRPAACGRMRGAEGAKPRGRQAK-----------------------------------AARAPPGQG
ZmARGOS_5_pep    (29)   LAAAAAAAGVPAGSSTAATA-----------------------------------------T
ZmARGOS_6_pep     (1)   ----------------------------------------------------------------
ZmARGOS_7_pep    (16)   AAHGGRHKHDDDDPSTPR-------------------------------------------GFCAK
ZmARGOS_8_pep    (14)   ARALALGQVSVMRAMPQE-------------------------------------------EEAAVATTT
ZmARGOS_9_pep    (35)   CRKSDAAVAKGQQRQNASP------------------------------------------PSPKPPPAG
GmARGOS_1_pep     (6)   PRDQVGGETHKNLVEPNVAAS----------------------------------------KKARNCA
GmARGOS_2_pep     (6)   PRDQVGGDTHKNLVAPNVAAS----------------------------------------KKARNCA
GmARGOS_3_pep     (1)   ----------------------------------------------------------------MAR
GmARGOS_4_pep     (1)   ----------------------------------------------------------------MAR
GmARGOS_5_pep     (1)   --MSSWLIHYNKRFIISIS------------------------------------------LAFMLR
SbARGOS_1_pep    (32)   MESG-GGSASSPRASTSDRRLQRAAHSHREEWEPAAAASGDGGTGSLWSR
SbARGOS_2_pep    (19)   NNAVKRHLQQ--RQQEADF------------------------------------------HDKKVIAST
SbARGOS_3_pep     (1)   -NAVKRHLQQ--RQQEADF------------------------------------------HDKKVIAST
SbARGOS_4_pep     (1)   ----------------------------------------------------------------
SbARGOS_5_pep    (51)   RRGAMHGAAEQQKQQQQRGRPQ---------------------------GTRAAPPVPPG
SbARGOS_6_pep    (26)   EGGS------GKMRGRQATKAR----P----------------------VVLAPPGQG
SbARGOS_7_pep     (1)   ------MRRAVPQEE----------------------------------AVAAATTTT
SbARGOS_8_pep    (15)   TAHGGWHKHDD--PSTPR-------------------------------------------GFCTK
SbARGOS_9_pep     (1)   ----------------------------------------------------------------M
Consensus        (51)
```

```
                151                                                         196
AtARGOS_1A_pep   (89) FMPSHSNANTDVTCNFM---------------------------------
AtARGOS_1B_pep  (113) FMPSHSNANTDVTCNFM---------------------------------
AtARGOS_2_pep   (119) FMPSNS-KHVSSSSTFM---------------------------------
AtARGOS_3_pep    (73) FSPSNEPSLAVEPLDP----------------------------------
OsARGOS_1_pep    (99) LFPVQ---------------------------------------------
OsARGOS_2_pep    (46) FLPNRDVVVYGQQPAADQFFFRQ---------------------------
OsARGOS_3_pep   (132) FVPLDAQSNVVGSSCL----------------------------------
OsARGOS_4_pep   (100) FMPTTSSSSAGGGGGGGRNGA------------------TTGHAPYL-
OsARGOS_5_pep   (103) VLLPSDAKSIAAAGRPSSSSSSYL--------------------------
OsARGOS_6_pep    (61) FFPAAGSDGVVAAAAVAGTYQPPPPPARSSPPPSSSSSSSRQL-------
OsARGOS_7_pep    (92) -FMPTDVRSMASSYL-----------------------------------
OsARGOS_8_pep   (104) -FMPIDMRTMASSYFFCL--------------------------------
ZmARGOS_1_pep   (129) FMPTSTG-----GRGGTG-------------------------PTYM--
ZmARGOS_2_pep   (127) FMPTSTG-----GRGGTG-------------------------PTYM--
ZmARGOS_3_pep    (92) -FMPTDVRSMASSYL-----------------------------------
ZmARGOS_4_pep   (132) ALVPSDGRAAAAVASSCVC-------------------------------
ZmARGOS_5_pep    (99) VLLPSDARAAVAT--P-TSSASYL--------------------------
ZmARGOS_6_pep    (49) FFPSNHCPCSSPTFTQ----------------------------------
ZmARGOS_7_pep    (88) LMP---AAAGGRNEAVDP-------------------------ASYL--
ZmARGOS_8_pep    (90) FCPAATSS---PSPMHAADHG------------------SFGTTGSPHLC
ZmARGOS_9_pep   (112) TFVPSDVRSMPSSNL-----------------------------------
GmARGOS_1_pep    (83) FSPSTLPNMAVLTS------------------------------------
GmARGOS_2_pep    (83) FSPSILPNMAVLTS------------------------------------
GmARGOS_3_pep    (53) FSPSDQNGVVYAST------------------------------------
GmARGOS_4_pep    (53) FSPSDQNGVVYATT------------------------------------
GmARGOS_5_pep    (73) LYSKHGPADVIYQCNFTW--------------------------------
SbARGOS_1_pep   (129) FMPTSVR----AGTGTG--------------------------PTYM--
SbARGOS_2_pep    (94) -FMPTDVRSVAASYL-----------------------------------
SbARGOS_3_pep    (75) -FMPTDVRSMASSYL-----------------------------------
SbARGOS_4_pep    (43) LFPSHHCACSSPTFTQ----------------------------------
SbARGOS_5_pep   (133) FVPLDAHSHLVVGSSR----------------------------------
SbARGOS_6_pep   (101) ALVPSDGRAATAAVASS-CVC-----------------------------
SbARGOS_7_pep    (68) FCPTAASSGGGKSKLADADHGS-----------------SFRTTGSPHLR
SbARGOS_8_pep    (85) LMPVAAAAGARNEVVDP--------------------------ASYL--
SbARGOS_9_pep    (52) FLPTRDDDDAIAIYGSLRSVQ-----------------------------
      Consensus (151) F P S
```

FIGURE 2D

```
                                       1                                                 50
AtARGOS_1A SEQ ID NO: 26 (32-147)      ------------------------------MDVGRNNRKNMSFRSSPEK
           ZmARGOS1 SEQ ID NO: 2  (1)  MSTTRPEDTQQLINSAAAASPNRSAPSAAPSDMERGSGTAASSSRASTTSH
           ZmARGOS2 SEQ ID NO: 4  (1)  ------------------------------MASRSSAMEGGAAIQRNAVKR
           ZmARGOS3 SEQ ID NO: 6  (1)  -MSAGPEDTQQLINSAAAASPNRSAPSAAPSDMERGSGTAASSSRASTTSH
                    Consensus     (1)  S  PEDTQQLINSAAAASPNRSAPSAAPSDMERGSGTAASSSRRSTTSH 51                                                100
AtARGOS_1A SEQ ID NO: 26 (32-147) (20) SKQ------ELRRSFSAQKRMMIPANYFLESLFLIVGLIASLLIL
           ZmARGOS1 SEQ ID NO: 2  (51) SHQRATHRVVEEEEEEPSSSRGGGSLCSGYLSLP-ALLIVGVASIVIL
           ZmARGOS2 SEQ ID NO: 4  (23) HLQ-------QRQQEADFLDKKVIASTFSIGAFLVIACLIVSLLIL
           ZmARGOS3 SEQ ID NO: 6  (50) SHQRATHRVVEEEEE-PSSSRGAGSLCSGYLSLP-ALLVGVIASIVIL
                    Consensus    (51)  SHQRATHRVVEEEEEE PSSSRGKGSICSGYLSLPAALLLVGLTASLLIL 101                                               147
AtARGOS_1A SEQ ID NO: 26 (32-147) (60) PLVLPPLPPPFMLLLVPIGIMVILVLVLAFMPSSHSNANTDVTCNEM
           ZmARGOS1 SEQ ID NO: 2 (100) PLVLPPLPPPPSMIMLVPVAMLLLLVLAFMPTSSTGRGTGPTYM
           ZmARGOS2 SEQ ID NO: 4  (63) PLVIPPLPPPPSLIIMLVCHIMTILVLAFMPTDVRSMASSYL---
           ZmARGOS3 SEQ ID NO: 6  (98) PLVIPPLPPPPSLIMLVPVAMLILLVLAFMPTSSTGRGTGPTYM
                    Consensus   (101)  PLVLPPLPPPSLLLLVPVAMLLLLVLAFMPTSSTGRGTGPTYM
```

FIGURE 3

ZEA MAIZE AUXIN RESPONSE RELATED GENES FOR CONTROLLING PLANT GROWTH AND ORGAN SIZE AND THEIR USE IN IMPROVING CROP PLANTS

CROSS REFERENCE

This application is a continuation of U.S. Utility application Ser. No. 12/464,144 now issued as U.S. Pat. No. 7,934,240, filed May 12, 2009, which is a continuation of U.S. Utility application Ser. No. 11/692,977 filed Mar. 29, 2007, and also claims the benefit U.S. Provisional Patent Application No. 60/788,123, filed Mar. 31, 2006, all of which are incorporated herein by reference.

FIELD OF THE INVENTION

The invention relates generally to the field of molecular biology.

BACKGROUND OF THE INVENTION

The domestication of many plants has correlated with dramatic increases in yield. Most phenotypic variation occurring in natural populations is continuous and is effected by multiple gene influences. The identification of specific genes responsible for the dramatic differences in yield, in domesticated plants, has become an important focus of agricultural research.

In *Arabidopsis*, one family of genes associated with plant changes that relate to improved yield in crops, the (ARGOS) Auxin-Regulated Gene involved in Organ Size gene is inducible by auxin. This gene is responsible for the regulation of cell proliferation and organ growth. The *Arabidopsis* ARGOS is naturally expressed at a low level in various young tissues including roots, inflorescence stems, flower, young rosette leaves and silliques, but undetectable in mature leaves. In studies by Hu, et al., (2003 *Plant Cell* 15:1951-61) and Hu, et al., (2006 *The Plant Journal* 47(1):1-9), transgenic plants that ectopically over-express sense or antisense ARGOS cDNA display enlarged or reduced aerial organs, respectively. Alteration in organ size demonstrate in these plants is associated with changes in cell number and not cell size. The increased cell number is attributed to the duration of organ growth in *Arabidopsis*.

The present invention includes the identification of the putative maize ARGOS genes, ZmARGOS 1-9 (SEQ ID NOS: 1, 3, 5, 40-45 and 71) that are related to the *Arabidopsis* ARGOS genes (SEQ ID NOS: 59, 60 and 61). The ortholog having the most similarity to *Arabidopsis* ARGOS (SEQ ID NO: 59), is ZmARGOS 1 (SEQ ID NO: 1). ZmARGOS 1 and 2 (SEQ ID NOS: 1 and 3) expression in maize was primarily in the roots, early endosperm, immature ear and shoot and ear inflorescent meristems. The expression is associated with actively growing tissues, and is found to a lesser degree in the mature tissues. This finding is consistent with the noted positive effect of the gene on regulating growth and cell proliferation. The ZmARGOS 3 gene (SEQ ID NO: 5) expressed in a wide spectrum of tissues and developmental stages.

Transgenic plants expressing ZmARGOS 1 (SEQ ID NO: 1) show a positive impact on biomass accumulation and rate of maize plant growth, as well as an increase in organ size. These maize genes will find utility for enhancing agronomic traits in maize (and other crops).

The present invention also includes the identification of ARGOS genes in other plant species. The rice gene family is represented by 8 family members. Nine members of the gene family were found in *Sorghum bicolor*. Five gene sequences were also found in Soybean (*Glycine max*). Three members of the ARGOS *Arabidopsis* gene family are disclosed herein.

BRIEF SUMMARY OF THE INVENTION

Compositions and methods for controlling plant growth and organ size for increasing yield in a plant are provided. The compositions include ARGOS sequences from maize, soybean, *arabidopsis*, rice and sorghum. Compositions of the invention comprise amino acid sequences and nucleotide sequences selected from SEQ ID NOS: 1-37, 40-71 as well as variants and fragments thereof.

Polynucleotides encoding the ARGOS sequences are provided in DNA constructs for expression in a plant of interest. Expression cassettes, plants, plant cells, plant parts and seeds comprising the sequences of the invention are further provided. In specific embodiments, the polynucleotide is operably linked to a constitutive promoter.

Methods for modulating the level of an ARGOS sequence in a plant or plant part is provided. The methods comprise introducing into a plant or plant part a heterologous polynucleotide comprising an ARGOS sequence of the invention. The level of ARGOS polypeptide can be increased or decreased. Such method can be used to increase the yield in plants; in one embodiment, the method is used to increase grain yield in cereals.

BRIEF DESCRIPTION OF THE DRAWINGS

FIG. 2: Alignment of the maize, rice, soybean, sorghum and *arabidopsis* polypeptide sequences with identification of conserved regions. The proteins have a well-conserved proline-rich region near the C-terminus. The N-termini are generally diverged. The proteins are quite short, ranging from 58 to 146, and averaging 110 amino acids.

FIG. 3: Alignment of ZmARGOS 1, 2 and 3, with AtARGOS 1, highlighting their areas of consensus, and conservative substitutions.

DETAILED DESCRIPTION OF THE INVENTION

Figure 1:
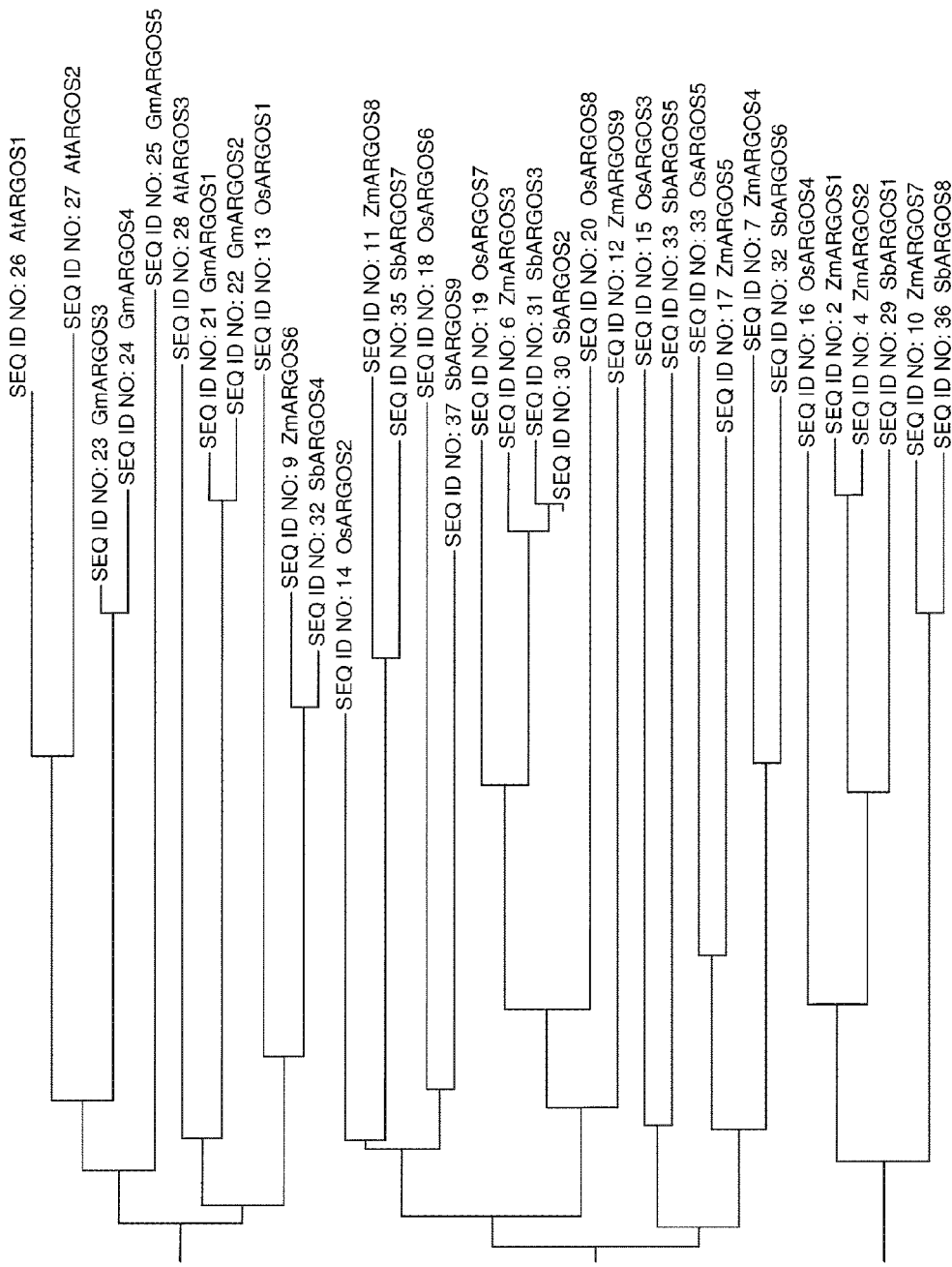
FIG. 1: Dendrogram illustrating the relationship between the ARGOS polypeptides of this invention from various plant species: maize, rice, soybean, sorghum and *arabidopsis*.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, BOTANY: PLANT BIOLOGY AND ITS RELATION TO HUMAN AFFAIRS, John Wiley (1982); CELL CULTURE AND SOMATIC CELL GENETICS OF PLANTS, vol. 1, Vasil, ed. (1984); Stanier, et al., THE MICROBIAL WORLD, 5$^{th}$ ed., Prentice-Hall (1986); Dhringra and Sinclair, BASIC PLANT PATHOLOGY METHODS, CRC Press (1985); Maniatis, et al., MOLECULAR CLONING: A LABORATORY MANUAL (1982); DNA CLONING, vols. I and II, Glover, ed. (1985); OLIGONUCLEOTIDE SYNTHESIS, Gait, ed. (1984); NUCLEIC ACID HYBRIDIZATION, Hames and Higgins, eds. (1984); and the series METHODS IN ENZYMOLOGY, Colowick and Kaplan, eds, Academic Press, Inc., San Diego, Calif.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), O-Beta Replicase systems, transcription-based amplification system (TAS) and strand displacement amplification (SDA). See, e.g., DIAGNOSTIC MOLECULAR MICROBIOLOGY: PRINCIPLES AND APPLICATIONS, Persing, et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) *J. Gen. Microbiol.* 139:425-32) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90%, preferably 60-90% of the native protein for it's native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). See also, Creighton, PROTEINS, W.H. Freeman and Co. (1984).

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolumn* (Yamao, et al., (1985) *Proc. Natl. Acad. Sci. USA* 82:2306-9) or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which contains a vector and supports the replication and/or expression of the expression vector. Host cells may be prokaryotic cells such as *E. coli*, or eukaryotic cells such as yeast, insect, plant, amphibian or mammalian cells. Preferably, host cells are monocotyledonous or dicotyledonous plant cells, including but not limited to maize, sorghum, sunflower, soybean, wheat, alfalfa, rice, cotton, canola, barley, millet and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids. Unless otherwise stated, the term "ARGOS nucleic acid" means a nucleic acid comprising a polynucleotide ("ARGOS polynucleotide") encoding a ARGOS polypeptide.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, GUIDE TO MOLECULAR CLONING TECHNIQUES, from the series METHODS IN ENZYMOLOGY, vol. 152, Academic Press, Inc., San Diego, Calif. (1987); Sambrook, et al., MOLECULAR CLONING: A LABORATORY MANUAL, $2^{nd}$ ed., vols. 1-3 (1989); and CURRENT PROTOCOLS 1N MOLECULAR BIOLOGY, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. A particularly preferred plant is *Zea mays*.

As used herein, "yield" includes reference to bushels per acre of a grain crop at harvest, as adjusted for grain moisture (15% typically). Grain moisture is measured in the grain at harvest. The adjusted test weight of grain is determined to be the weight in pounds per bushel, adjusted for grain moisture level at harvest.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions.

The term "ARGOS polypeptide" refers to one or more amino acid sequences. The term is also inclusive of fragments, variants, homologs, alleles or precursors (e.g., preproproteins or proproteins) thereof. A "ARGOS protein" comprises a ARGOS polypeptide. Unless otherwise stated, the term "ARGOS nucleic acid" means a nucleic acid comprising a polynucleotide ("ARGOS polynucleotide") encoding a ARGOS polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus or nucleic acid fragment. Typically, the recombinant expression cassette portion of an expression vector includes, among other sequences, a nucleic acid to be transcribed and a promoter.

The term "residue" or "amino acid residue" or "amino acid" are used interchangeably herein to refer to an amino acid that is incorporated into a protein, polypeptide or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C. and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.* 138:267-84: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part I, chapter 2, "Overview of principles of hybridization and the strategy of nucleic acid probe assays," Elsevier, New York (1993); and CURRENT PROTOCOLS IN MOLECULAR BIOLOGY, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA and 25 mM Na phosphate at 65° C., and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence", (b) "comparison window", (c) "sequence identity", (d) "percentage of sequence identity" and (e) "substantial identity".

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches. Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package®, Version 8 (available from Genetics Computer Group (GCG®) programs (Accelrys, Inc., San Diego, Calif.)). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65 and Pearson, et al., (1994) *Meth. Mol. Biol.* 24:307-31. The preferred program to use for optimal global alignment of multiple sequences is PileUp (Feng and Doolittle, (1987) *J. Mol. Evol.*, 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences and TBLASTX for nucleotide query sequences against nucleotide database sequences. See, CURRENT PROTOCOLS IN MOLECULAR BIOLOGY, Chapter 19, Ausubel, et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package® are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package® is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

The invention discloses ARGOS polynucleotides and polypeptides. The novel nucleotides and proteins of the invention have an expression pattern which indicates that they regulate cell number and thus play an important role in plant development. The polynucleotides are expressed in various plant tissues. The polynucleotides and polypeptides thus provide an opportunity to manipulate plant development to alter seed and vegetative tissue development, timing or composition. This may be used to create a sterile plant, a seedless plant or a plant with altered endosperm composition.

Nucleic Acids

The present invention provides, inter alia, isolated nucleic acids of RNA, DNA and analogs and/or chimeras thereof, comprising a ARGOS polynucleotide.

The present invention also includes polynucleotides optimized for expression in different organisms. For example, for expression of the polynucleotide in a maize plant, the sequence can be altered to account for specific codon preferences and to alter GC content as according to Murray, et al., supra. Maize codon usage for 28 genes from maize plants is listed in Table 4 of Murray, et al., supra.

The ARGOS nucleic acids of the present invention comprise isolated ARGOS polynucleotides which are inclusive of:
(a) a polynucleotide encoding a ARGOS polypeptide and conservatively modified and polymorphic variants thereof;
(b) a polynucleotide having at least 70% sequence identity with polynucleotides of (a) or (b);
(c) complementary sequences of polynucleotides of (a) or (b).

The following table, Table 1, lists the specific identities of the polynucleotides and polypeptides and disclosed herein.

TABLE 1

| Gene name | Plant species | Polynucleotide/Polypeptide | SEQ ID NO: |
|---|---|---|---|
| ZmARGOS1 | Zea mays | Polynucleotide | SEQ ID NO: 1 |
|  |  | Polypeptide | SEQ ID NO: 2 |
|  |  | Genomic sequence | SEQ ID NO: 71 |
| ZmARGOS2 | Zea mays | Polynucleotide | SEQ ID NO: 3 |
|  |  | Polypeptide | SEQ ID NO: 4 |
| ZmARGOS3 | Zea mays | Polypeptide | SEQ ID NO: 5 |
|  |  | Polynucleotide | SEQ ID NO: 6 |
| ZmARGOS4 | Zea mays | Polypeptide | SEQ ID NO: 7 |
|  |  | Polynucleotide | SEQ ID NO: 40 |
| ZmARGOS5 | Zea mays | Polypeptide | SEQ ID NO: 8 |
|  |  | Polynucleotide | SEQ ID NO: 41 |
| ZmARGOS6 | Zea mays | Polypeptide | SEQ ID NO: 9 |
|  |  | Polynucleotide | SEQ ID NO: 42 |
| ZmARGOS7 | Zea mays | Polypeptide | SEQ ID NO: 10 |
|  |  | Polynucleotide | SEQ ID NO: 43 |
| ZmARGOS8 | Zea mays | Polypeptide | SEQ ID NO: 11 |
|  |  | Polynucleotide | SEQ ID NO: 44 |
| ZmARGOS9 | Zea mays | Polypeptide | SEQ ID NO: 12 |
|  |  | Polynucleotide | SEQ ID NO: 45 |
| OsARGOS1 | Oryza sativa | Polypeptide | SEQ ID NO: 13 |
|  |  | Polynucleotide | SEQ ID NO: 46 |
| OsARGOS2 | Oryza sativa | Polypeptide | SEQ ID NO: 14 |
|  |  | Polynucleotide | SEQ ID NO: 47 |
| OsARGOS3 | Oryza sativa | Polypeptide | SEQ ID NO: 15 |
|  |  | Polynucleotide | SEQ ID NO: 48 |
| OsARGOS4 | Oryza sativa | Polypeptide | SEQ ID NO: 16 |
|  |  | Polynucleotide | SEQ ID NO: 49 |
| OsARGOS5 | Oryza sativa | Polypeptide | SEQ ID NO: 17 |
|  |  | Polynucleotide | SEQ ID NO: 50 |
| OsARGOS6 | Oryza sativa | Polypeptide | SEQ ID NO: 18 |
|  |  | Polynucleotide | SEQ ID NO: 51 |
| OsARGOS7 | Oryza sativa | Polypeptide | SEQ ID NO: 19 |
|  |  | Polynucleotide | SEQ ID NO: 52 |
| OsARGOS8 | Oryza sativa | Polypeptide | SEQ ID NO: 20 |
|  |  | Polynucleotide | SEQ ID NO: 53 |
| GmARGOS1 | Glycine max | Polypeptide | SEQ ID NO: 21 |
|  |  | Polynucleotide | SEQ ID NO: 54 |
| GmARGOS2 | Glycine max | Polypeptide | SEQ ID NO: 22 |
|  |  | Polynucleotide | SEQ ID NO: 55 |
| GmARGOS3 | Glycine max | Polypeptide | SEQ ID NO: 23 |
|  |  | Polynucleotide | SEQ ID NO: 56 |
| GmARGOS4 | Glycine max | Polypeptide | SEQ ID NO: 24 |
|  |  | Polynucleotide | SEQ ID NO: 57 |
| GmARGOS5 | Glycine max | Polypeptide | SEQ ID NO: 25 |
|  |  | Polynucleotide | SEQ ID NO: 58 |
| SbARGOS1 | Sorghum bicolor | Polypeptide | SEQ ID NO: 29 |
|  |  | Polynucleotide | SEQ ID NO: 62 |
| SbARGOS2 | Sorghum bicolor | Polypeptide | SEQ ID NO: 30 |
|  |  | Polynucleotide | SEQ ID NO: 63 |
| SbARGOS3 | Sorghum bicolor | Polypeptide | SEQ ID NO: 31 |
|  |  | Polynucleotide | SEQ ID NO: 64 |
| SbARGOS4 | Sorghum bicolor | Polypeptide | SEQ ID NO: 32 |
|  |  | Polynucleotide | SEQ ID NO: 65 |
| SbARGOS5 | Sorghum bicolor | Polypeptide | SEQ ID NO: 33 |
|  |  | Polynucleotide | SEQ ID NO: 66 |
| SbARGOS6 | Sorghum bicolor | Polypeptide | SEQ ID NO: 34 |
|  |  | Polynucleotide | SEQ ID NO: 67 |
| SbARGOS7 | Sorghum bicolor | Polypeptide | SEQ ID NO: 35 |
|  |  | Polynucleotide | SEQ ID NO: 68 |

TABLE 1-continued

| Gene name | Plant species | Polynucleotide/Polypeptide | SEQ ID NO: |
|---|---|---|---|
| SbARGOS8 | Sorghum bicolor | Polypeptide | SEQ ID NO: 36 |
| | | Polynucleotide | SEQ ID NO: 69 |
| SbARGOS9 | Sorghum bicolor | Polypeptide | SEQ ID NO: 37 |
| | | Polynucleotide | SEQ ID NO: 70 |
| AtARGOS1 | Arabidopsis thaliana | Polypeptide | SEQ ID NO: 26 |
| | | Polynucleotide | SEQ ID NO: 59 |
| AtARGOS2 | Arabidopsis thaliana | Polypeptide | SEQ ID NO: 27 |
| | | Polynucleotide | SEQ ID NO: 60 |
| AtARGOS3 | Arabidopsis thaliana | Polypeptide | SEQ ID NO: 28 |
| | | Polynucleotide | SEQ ID NO: 61 |
| Primer | Artificial sequence | Polynucleotide | SEQ ID NO: 38 |
| Primer | Artificial sequence | Polynuceotide | SEQ ID NO: 39 |

Construction of Nucleic Acids

The isolated nucleic acids of the present invention can be made using (a) standard recombinant methods, (b) synthetic techniques or combinations thereof. In some embodiments, the polynucleotides of the present invention will be cloned, amplified or otherwise constructed from a fungus or bacteria.

The nucleic acids may conveniently comprise sequences in addition to a polynucleotide of the present invention. For example, a multi-cloning site comprising one or more endo-nuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter or linker for cloning and/or expression of a polynucleotide of the present invention. Additional sequences may be added to such cloning and/or expression sequences to optimize their function in cloning and/or expression, to aid in isolation of the polynucleotide or to improve the introduction of the polynucleotide into a cell. Typically, the length of a nucleic acid of the present invention less the length of its polynucleotide of the present invention is less than 20 kilobase pairs, often less than 15 kb and frequently less than 10 kb. Use of cloning vectors, expression vectors, adapters and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSSlox and lambda MOSElox. Optional vectors for the present invention, include but are not limited to, lambda ZAP II and pGEX. For a description of various nucleic acids see, e.g., Stratagene Cloning Systems, Catalogs 1995, 1996, 1997 (La Jolla, Calif.) and, Amersham Life Sciences, Inc, Catalog '97 (Arlington Heights, Ill.).

Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphora-midite method of Beaucage, et al., (1981) *Tetra. Letts.* 22(20): 1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68 and the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G> 7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' UTR regions for modulation of translation of heter-ologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group. See, Devereaux, et al., (1984) *Nucleic Acids Res.* 12:387-395; or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuf-fling using polynucleotides of the present invention, and compositions resulting therefrom. Sequence shuffling is described in PCT Publication Number 96/19256. See also, Zhang, et al., (1997) *Proc. Natl. Acad. Sci. USA* 94:4504-9 and Zhao, et al., (1998) *Nature Biotech* 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation or other expression property of a gene or transgene, a replicative element, a protein-binding element or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a polypeptide long enough to code for an active protein of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683, 439), the Nos promoter, the rubisco promoter, the GRP1-8 promoter, the 35S promoter from cauliflower mosaic virus (CaMV), as described in Odell, et al., (1985) *Nature* 313:810-2; rice actin (McElroy, et al., (1990) *Plant Cell* 163-171); ubiquitin (Christensen, et al., (1992) *Plant Mol. Biol.* 12:619-632 and Christensen, et al., (1992) *Plant Mol. Biol.* 18:675-89); pEMU (Last, et al., (1991) *Theor. Appl. Genet.* 81:581-8); MAS (Velten, et al., (1984) *EMBO J.* 3:2723-30) and maize H3 histone (Lepetit, et al., (1992) *Mol. Gen. Genet.* 231:276-85 and Atanassvoa, et al., (1992) *Plant Journal* 2(3): 291-300); ALS promoter, as described in PCT Application Number WO 96/30530; GOS2 (U.S. Pat. No. 6,504,083) and other transcription initiation regions from various plant genes known to those of skill. For the present invention ubiquitin is the preferred promoter for expression in monocot plants.

Alternatively, the plant promoter can direct expression of a polynucleotide of the present invention in a specific tissue or may be otherwise under more precise environmental or developmental control. Such promoters are referred to here as "inducible" promoters (Rab17, RAD29). Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light.

Examples of promoters under developmental control include promoters that initiate transcription only, or preferentially, in certain tissues, such as leaves, roots, fruit, seeds or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes or alternatively from another plant gene or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) *Nucleic Acids Res.* 12:369-85); the potato proteinase inhibitor II (PINII) gene (Keil, et al., (1986) *Nucleic Acids Res.* 14:5641-50 and An, et al., (1989) *Plant Cell* 1:115-22) and the CaMV 19S gene (Mogen, et al., (1990) *Plant Cell* 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) *Mol. Cell. Biol.* 8:4395-4405; Callis, et al., (1987) *Genes Dev.* 1:1183-200). Such intron enhancement of gene expression is typically greatest when placed near the 5' end of the transcription unit. Use of maize introns Adh1-S intron 1, 2, and 6, the Bronze-1 intron are known in the art. See generally, THE MAIZE HANDBOOK, Chapter 116, Freeling and Walbot, eds., Springer, New York (1994).

Plant signal sequences, including, but not limited to, signal-peptide encoding DNA/RNA sequences which target proteins to the extracellular matrix of the plant cell (Dratewka-Kos, et al., (1989) *J. Biol. Chem.* 264:4896-900), such as the *Nicotiana* plumbaginifolia extension gene (DeLoose, et al., (1991) *Gene* 99:95-100); signal peptides which target proteins to the vacuole, such as the sweet potato sporamin gene (Matsuka, et al., (1991) *Proc. Natl. Acad. Sci. USA* 88:834) and the barley lectin gene (Wilkins, et al., (1990) *Plant Cell,* 2:301-13); signal peptides which cause proteins to be secreted, such as that of PRIb (Lind, et al., (1992) *Plant Mol. Biol.* 18:47-53) or the barley alpha amylase (BAA) (Rahmatullah, et al., (1989) *Plant Mol. Biol.* 12:119 and hereby incorporated by reference) or signal peptides which target proteins to the plastids such as that of rapeseed enoyl-Acp reductase (Verwaert, et al., (1994) *Plant Mol. Biol.* 26:189-202) are useful in the invention. The barley alpha amylase signal sequence fused to the ARGOS polynucleotide is the preferred construct for expression in maize for the present invention.

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene) or other such genes known in the art. The bar gene encodes resistance to the herbicide basta and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers, et al., (1987) *Meth. Enzymol.* 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11 and Berger, et al., (1989) *Proc. Natl. Acad. Sci. USA,* 86:8402-6. Another useful vector herein is plasmid pBI101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian or preferably plant cells. The cells produce the protein in a non-natural condition (e.g., in quantity, composition, location and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level" or about 1/10 transcripts to about 1/100 transcripts to about 1/1,000 transcripts.

One of skill would recognize that modifications could be made to a protein of the present invention without diminishing its biological activity. Some modifications may be made to facilitate the cloning, expression or incorporation of the targeting molecule into a fusion protein. Such modifications are well known to those of skill in the art and include, for example, a methionine added at the amino terminus to provide an initiation site or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., (1982) METHODS IN YEAST GENETICS, Cold Spring Harbor Laboratory is a well recognized work describing the various methods available to produce the protein in yeast. Two widely utilized yeasts for production of eukaryotic proteins are *Saccharomyces cerevisiae* and *Pichia pastoris*. Vectors, strains and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase and an origin of replication, termination sequences and the like as desired.

A protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect or plant origin. Mammalian cell systems often will be in the form of monolayers of cells although mammalian cell suspensions may also be used. A number of suitable host cell lines capable of expressing intact proteins have been developed in the art, and include the HEK293, BHK21 and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49) and necessary processing information sites, such as ribosome binding sites, RNA splice sites, polyadenylation sites (e.g., an SV40 large T Ag poly A addition site) and transcriptional terminator sequences. Other animal cells useful for production of proteins of the present invention are available, for instance, from the American Type Culture Collection Catalogue of Cell Lines and Hybridomas (7$^{th}$ ed., 1992).

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (see, e.g., Schneider, (1987) *J. Embryol. Exp. Morphol.* 27:353-65).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., (1983) *J. Virol.* 45:773-81). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in DNA CLONING: A PRACTICAL APPROACH, vol. II, Glover, ed., IRL Press, Arlington, Va., pp. 213-38 (1985)).

In addition, the gene for ARGOS placed in the appropriate plant expression vector can be used to transform plant cells. The polypeptide can then be isolated from plant callus or the transformed cells can be used to regenerate transgenic plants. Such transgenic plants can be harvested and the appropriate tissues (seed or leaves, for example) can be subjected to large scale protein extraction and purification techniques.

Plant Transformation Methods

Numerous methods for introducing foreign genes into plants are known and can be used to insert a ARGOS polynucleotide into a plant host, including biological and physical plant transformation protocols. See, e.g., Miki, et al., "Procedure for Introducing Foreign DNA into Plants," in METHODS IN PLANT MOLECULAR BIOLOGY AND BIOTECHNOLOGY, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch, et al., (1985) *Science* 227:1229-31), electroporation, micro-injection and biolistic bombardment.

Expression cassettes and vectors and in vitro culture methods for plant cell or tissue transformation and regeneration of plants are known and available. See, e.g., Gruber, et al., "Vectors for Plant Transformation," in METHODS IN PLANT MOLECULAR BIOLOGY AND BIOTECHNOLOGY, supra, pp. 89-119.

The isolated polynucleotides or polypeptides may be introduced into the plant by one or more techniques typically used for direct delivery into cells. Such protocols may vary depending on the type of organism, cell, plant or plant cell, i.e., monocot or dicot, targeted for gene modification. Suitable methods of transforming plant cells include microinjection (Crossway, et al., (1986) *Biotechniques* 4:320-334 and U.S. Pat. No. 6,300,543), electroporation (Riggs, et al., (1986) *Proc. Natl. Acad. Sci. USA* 83:5602-5606, direct gene transfer (Paszkowski, et al., (1984) *EMBO J.* 3:2717-2722) and ballistic particle acceleration (see, for example, Sanford, et al., U.S. Pat. No. 4,945,050; WO 91/10725 and McCabe, et al., (1988) *Biotechnology* 6:923-926). Also see, Tomes, et al., Direct DNA Transfer into Intact Plant Cells Via Microprojectile Bombardment. pp. 197-213 in Plant Cell, Tissue and Organ Culture, Fundamental Methods eds. Gamborg and Phillips, Springer-Verlag Berlin Heidelberg New York, 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839 and Gordon-Kamm, et al., (1990) *Plant Cell* 2:603-618 (maize); Hooydaas-Van Slogteren and Hooykaas, (1984) *Nature* (London) 311:763-764; Bytebier, et al., (1987) *Proc. Natl. Acad. Sci. USA* 84:5345-5349 (Liliaceae); De Wet, et al., (1985) In The Experimental Manipulation of Ovule Tissues, ed. Chapman, et al., pp. 197-209; Longman, N.Y. (pollen); Kaeppler, et al., (1990) *Plant Cell Reports* 9:415-418; and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001) *J Exp Bot* 52:1135-42); polyethylene glycol methods (Krens, et al., (1982) *Nature* 296:72-77);

protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185), all of which are herein incorporated by reference.

Agrobacterium-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. Pat. No. 913,914, filed Oct. 1, 1986, as referenced in U.S. Pat. No. 5,262,306, issued Nov. 16, 1993 and Simpson, et al., (1986) *Plant Mol. Biol.* 6:403-15 (also referenced in the '306 patent), all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms and a few monocotyledonous plants (e.g., certain members of the Liliales and Arales) are susceptible to infection with *A. tumefaciens*. *A. rhizogenes* also has a wide host range, embracing most dicots and some gymnosperms, which includes members of the Leguminosae, Compositae, and Chenopodiaceae. Monocot plants can now be transformed with some success. EP Patent Application Number 604 662 A1 discloses a method for transforming monocots using *Agrobacterium*. EP Patent Application Number 672 752 A1 discloses a method for transforming monocots with *Agrobacterium* using the scutellum of immature embryos. Ishida, et al., discuss a method for transforming maize by exposing immature embryos to *A. tumefaciens* (*Nature Biotechnology* 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra; and U.S. Pat. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206 and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731 and Christou, et al., (1987) *Proc. Natl. Acad. Sci. USA* 84:3962. Direct uptake of DNA into protoplasts using $CaCl_2$ precipitation, polyvinyl alcohol, or poly-L-ornithine has also been reported. See, e.g., Hain, et al., (1985) *Mol. Gen. Genet.* 199:161 and Draper, et al., (1982) *Plant Cell Physiol.* 23:451.

Electroporation of protoplasts and whole cells and tissues has also been described. See, e.g., Donn, et al., (1990) in *Abstracts of the VIIth Int'l. Congress on Plant Cell and Tissue Culture IAPTC, A*2-38, p. 53; D'Halluin, et al., (1992) *Plant Cell* 4:1495-505 and Spencer, et al., (1994) *Plant Mol. Biol.* 24:51-61.

Increasing the Activity and/or Level of a ARGOS Polypeptide

Methods are provided to increase the activity and/or level of the ARGOS polypeptide of the invention. An increase in the level and/or activity of the ARGOS polypeptide of the invention can be achieved by providing to the plant an ARGOS polypeptide. The ARGOS polypeptide can be provided by introducing the amino acid sequence encoding the ARGOS polypeptide into the plant, introducing into the plant a nucleotide sequence encoding an ARGOS polypeptide or alternatively by modifying a genomic locus encoding the ARGOS polypeptide of the invention.

As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide having cell number regulator activity. It is also recognized that the methods of the invention may employ a polynucleotide that is not capable of directing, in the transformed plant, the expression of a protein or an RNA. Thus, the level and/or activity of an ARGOS polypeptide may be increased by altering the gene encoding the ARGOS polypeptide or its promoter. See, e.g., Kmiec, U.S. Pat. No. 5,565,350; Zarling, et al., PCT/US93/03868. Therefore mutagenized plants that carry mutations in ARGOS genes, where the mutations increase expression of the ARGOS gene or increase the plant growth and/or organ development activity of the encoded ARGOS polypeptide are provided.

Reducing the Activity and/or Level of a ARGOS Polypeptide

Methods are provided to reduce or eliminate the activity of an ARGOS polypeptide of the invention by transforming a plant cell with an expression cassette that expresses a polynucleotide that inhibits the expression of the ARGOS polypeptide. The polynucleotide may inhibit the expression of the ARGOS polypeptide directly, by preventing translation of the ARGOS messenger RNA, or indirectly, by encoding a polypeptide that inhibits the transcription or translation of a ARGOS gene encoding a ARGOS polypeptide. Methods for inhibiting or eliminating the expression of a gene in a plant are well known in the art, and any such method may be used in the present invention to inhibit the expression of an ARGOS polypeptide.

In accordance with the present invention, the expression of a ARGOS polypeptide is inhibited if the protein level of the ARGOS polypeptide is less than 70% of the protein level of the same ARGOS polypeptide in a plant that has not been genetically modified or mutagenized to inhibit the expression of that ARGOS polypeptide. In particular embodiments of the invention, the protein level of the ARGOS polypeptide in a modified plant according to the invention is less than 60%, less than 50%, less than 40%, less than 30%, less than 20%, less than 10%, less than 5% or less than 2% of the protein level of the same ARGOS polypeptide in a plant that is not a mutant or that has not been genetically modified to inhibit the expression of that ARGOS polypeptide. The expression level of the ARGOS polypeptide may be measured directly, for example, by assaying for the level of ARGOS polypeptide expressed in the plant cell or plant, or indirectly, for example, by measuring the plant growth and/or organ development activity of the ARGOS polypeptide in the plant cell or plant or by measuring the biomass in the plant. Methods for performing such assays are described elsewhere herein.

In other embodiments of the invention, the activity of the ARGOS polypeptides is reduced or eliminated by transforming a plant cell with an expression cassette comprising a polynucleotide encoding a polypeptide that inhibits the activity of a ARGOS polypeptide. The plant growth and/or organ development activity of a ARGOS polypeptide is inhibited according to the present invention if the plant growth and/or organ development activity of the ARGOS polypeptide is less than 70% of the plant growth and/or organ development activity of the same ARGOS polypeptide in a plant that has not been modified to inhibit the plant growth and/or organ development activity of that ARGOS polypeptide. In particular embodiments of the invention, the plant growth and/or organ development activity of the ARGOS polypeptide in a modified plant according to the invention is less than 60%, less than 50%, less than 40%, less than 30%, less than 20%, less than 10% or less than 5% of the plant growth and/or organ development activity of the same ARGOS polypeptide in a plant that that has not been modified to inhibit the expression of that ARGOS polypeptide. The plant growth and/or organ development activity of an ARGOS polypeptide is "eliminated" according to the invention when it is not detectable by the assay methods described elsewhere herein. Methods of determining the plant growth and/or organ development activity of an ARGOS polypeptide are described elsewhere herein.

In other embodiments, the activity of an ARGOS polypeptide may be reduced or eliminated by disrupting the gene encoding the ARGOS polypeptide. The invention encompasses mutagenized plants that carry mutations in ARGOS genes, where the mutations reduce expression of the ARGOS gene or inhibit the plant growth and/or organ development activity of the encoded ARGOS polypeptide.

Thus, many methods may be used to reduce or eliminate the activity of an ARGOS polypeptide. In addition, more than one method may be used to reduce the activity of a single ARGOS polypeptide. Non-limiting examples of methods of reducing or eliminating the expression of ARGOS polypeptides are given below.

1. Polynucleotide-Based Methods:

In some embodiments of the present invention, a plant is transformed with an expression cassette that is capable of expressing a polynucleotide that inhibits the expression of an ARGOS polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one ARGOS polypeptide is an expression cassette capable of producing an RNA molecule that inhibits the transcription and/or translation of at least one ARGOS polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of an ARGOS polypeptide are given below.

i. Sense Suppression/Cosuppression

In some embodiments of the invention, inhibition of the expression of a ARGOS polypeptide may be obtained by sense suppression or cosuppression. For cosuppression, an expression cassette is designed to express an RNA molecule corresponding to all or part of a messenger RNA encoding an ARGOS polypeptide in the "sense" orientation. Over expression of the RNA molecule can result in reduced expression of the native gene. Accordingly, multiple plant lines transformed with the cosuppression expression cassette are screened to identify those that show the greatest inhibition of ARGOS polypeptide expression.

The polynucleotide used for cosuppression may correspond to all or part of the sequence encoding the ARGOS polypeptide, all or part of the 5' and/or 3' untranslated region of an ARGOS polypeptide transcript or all or part of both the coding sequence and the untranslated regions of a transcript encoding an ARGOS polypeptide. In some embodiments where the polynucleotide comprises all or part of the coding region for the ARGOS polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763 and U.S. Pat. Nos. 5,034,323, 5,283,184 and 5,942,657, each of which is herein incorporated by reference. The efficiency of cosuppression may be increased by including a poly-dT region in the expression cassette at a position 3' to the sense sequence and 5' of the polyadenylation signal. See, US Patent Application Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See U.S. Pat. Nos. 5,283,184 and 5,034,323, herein incorporated by reference.

ii. Antisense Suppression

In some embodiments of the invention, inhibition of the expression of the ARGOS polypeptide may be obtained by antisense suppression. For antisense suppression, the expression cassette is designed to express an RNA molecule complementary to all or part of a messenger RNA encoding the ARGOS polypeptide. Over expression of the antisense RNA molecule can result in reduced expression of the native gene. Accordingly, multiple plant lines transformed with the antisense suppression expression cassette are screened to identify those that show the greatest inhibition of ARGOS polypeptide expression.

The polynucleotide for use in antisense suppression may correspond to all or part of the complement of the sequence encoding the ARGOS polypeptide, all or part of the complement of the 5' and/or 3' untranslated region of the ARGOS transcript or all or part of the complement of both the coding sequence and the untranslated regions of a transcript encoding the ARGOS polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Application Publication Number 2002/0048814, herein incorporated by reference.

iii. Double-Stranded RNA Interference

In some embodiments of the invention, inhibition of the expression of a ARGOS polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of ARGOS polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743, and WO 99/49029, WO 99/53050, WO 99/61631 and WO 00/49035, each of which is herein incorporated by reference.

iv. Hairpin RNA Interference and Intron-Containing Hairpin RNA Interference

In some embodiments of the invention, inhibition of the expression of one or a ARGOS polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini, et al., *BMC Biotechnology* 3:7 and US Patent Application Publication Number 2003/0175965, each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing and this increases the efficiency of interference. See, for example, Smith, et al., (2000) *Nature* 407: 319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295 and US Patent Application Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the ARGOS polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,646,805, each of which is herein incorporated by reference.

vi. Ribozymes

In some embodiments, the polynucleotide expressed by the expression cassette of the invention is catalytic RNA or has ribozyme activity specific for the messenger RNA of the ARGOS polypeptide. Thus, the polynucleotide causes the degradation of the endogenous messenger RNA, resulting in reduced expression of the ARGOS polypeptide. This method is described, for example, in U.S. Pat. No. 4,987,071, herein incorporated by reference.

vii. Small Interfering RNA or Micro RNA

In some embodiments of the invention, inhibition of the expression of a ARGOS polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example, Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of ARGOS expression, the 22-nucleotide sequence is selected from a ARGOS transcript sequence and contains 22 nucleotides of said ARGOS sequence in sense orientation and 21 nucleotides of a corresponding antisense sequence that is complementary to the sense sequence. miRNA molecules are highly efficient at inhibiting the expression of endogenous genes and the RNA interference they induce is inherited by subsequent generations of plants.

2. Polypeptide-Based Inhibition of Gene Expression

In one embodiment, the polynucleotide encodes a zinc finger protein that binds to a gene encoding an ARGOS polypeptide, resulting in reduced expression of the gene. In particular embodiments, the zinc finger protein binds to a regulatory region of an ARGOS gene. In other embodiments, the zinc finger protein binds to a messenger RNA encoding an ARGOS polypeptide and prevents its translation. Methods of selecting sites for targeting by zinc finger proteins have been described, for example, in U.S. Pat. No. 6,453,242 and methods for using zinc finger proteins to inhibit the expression of genes in plants are described, for example, in US Patent Application Publication Number 2003/0037355, each of which is herein incorporated by reference.

3. Polypeptide-Based Inhibition of Protein Activity

In some embodiments of the invention, the polynucleotide encodes an antibody that binds to at least one ARGOS polypeptide and reduces the cell number regulator activity of the ARGOS polypeptide. In another embodiment, the binding of the antibody results in increased turnover of the antibody-ARGOS complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of an ARGOS polypeptide is reduced or eliminated by disrupting the gene encoding the ARGOS polypeptide. The gene encoding the ARGOS polypeptide may be disrupted by any method known in the art. For example, in one embodiment, the gene is disrupted by transposon tagging. In another embodiment, the gene is disrupted by mutagenizing plants using random or targeted mutagenesis and selecting for plants that have reduced cell number regulator activity.

i. Transposon Tagging

In one embodiment of the invention, transposon tagging is used to reduce or eliminate the ARGOS activity of one or more ARGOS polypeptide. Transposon tagging comprises inserting a transposon within an endogenous ARGOS gene to reduce or eliminate expression of the ARGOS polypeptide. "ARGOS gene" is intended to mean the gene that encodes an ARGOS polypeptide according to the invention.

In this embodiment, the expression of one or more ARGOS polypeptide is reduced or eliminated by inserting a transposon within a regulatory region or coding region of the gene encoding the ARGOS polypeptide. A transposon that is within an exon, intron, 5' or 3' untranslated sequence, a promoter or any other regulatory sequence of a ARGOS gene may be used to reduce or eliminate the expression and/or activity of the encoded ARGOS polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-

84; Mena, et al., (1996) *Science* 274:1537-1540 and U.S. Pat. No. 5,962,764, each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis and fast neutron deletion mutagenesis used in a reverse genetics sense (with PCR) to identify plant lines in which the endogenous gene has been deleted. For examples of these methods see, Ohshima, et al., (1998) *Virology* 243: 472-481; Okubara, et al., (1994) *Genetics* 137:867-874 and Quesada, et al., (2000) *Genetics* 154:421-436, each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function (cell number regulator activity) of the encoded protein are well known in the art. Insertional mutations in gene exons usually result in null-mutants. Mutations in conserved residues are particularly effective in inhibiting the cell number regulator activity of the encoded protein. Conserved residues of plant ARGOS polypeptides suitable for mutagenesis with the goal to eliminate cell number regulator activity have been described. Such mutants can be isolated according to well-known procedures and mutations in different ARGOS loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more ARGOS polypeptide. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides and recombinogenic oligonucleobases. Such vectors and methods of use are known in the art. See, for example, U.S. Pat. Nos. 5,565,350; 5,731,181; 5,756,325; 5,760,012; 5,795,972 and 5,871,984, each of which are herein incorporated by reference. See also, WO 98/49350, WO 99/07865, WO 99/25821 and Beetham, et al., (1999) *Proc. Natl. Acad. Sci. USA* 96:8774-8778, each of which is herein incorporated by reference.

iii. Modulating Plant Growth and/or Organ Development Activity

In specific methods, the level and/or activity of a cell number regulator in a plant is increased by increasing the level or activity of the ARGOS polypeptide in the plant. Methods for increasing the level and/or activity of ARGOS polypeptides in a plant are discussed elsewhere herein. Briefly, such methods comprise providing a ARGOS polypeptide of the invention to a plant and thereby increasing the level and/or activity of the ARGOS polypeptide. In other embodiments, an ARGOS nucleotide sequence encoding an ARGOS polypeptide can be provided by introducing into the plant a polynucleotide comprising an ARGOS nucleotide sequence of the invention, expressing the ARGOS sequence, increasing the activity of the ARGOS polypeptide and thereby increasing the number of tissue cells in the plant or plant part. In other embodiments, the ARGOS nucleotide construct introduced into the plant is stably incorporated into the genome of the plant.

In other methods, the number of cells and biomass of a plant tissue is increased by increasing the level and/or activity of the ARGOS polypeptide in the plant. Such methods are disclosed in detail elsewhere herein. In one such method, an ARGOS nucleotide sequence is introduced into the plant and expression of said ARGOS nucleotide sequence decreases the activity of the ARGOS polypeptide and thereby increasing the plant growth and/or organ development in the plant or plant part. In other embodiments, the ARGOS nucleotide construct introduced into the plant is stably incorporated into the genome of the plant.

As discussed above, one of skill will recognize the appropriate promoter to use to modulate the level/activity of a plant growth and/or organ development polynucleotide and polypeptide in the plant. Exemplary promoters for this embodiment have been disclosed elsewhere herein.

Accordingly, the present invention further provides plants having a modified plant growth and/or organ development when compared to the plant growth and/or organ development of a control plant tissue. In one embodiment, the plant of the invention has an increased level/activity of the ARGOS polypeptide of the invention and thus has increased plant growth and/or organ development in the plant tissue. In other embodiments, the plant of the invention has a reduced or eliminated level of the ARGOS polypeptide of the invention and thus has decreased plant growth and/or organ development in the plant tissue. In other embodiments, such plants have stably incorporated into their genome a nucleic acid molecule comprising a ARGOS nucleotide sequence of the invention operably linked to a promoter that drives expression in the plant cell.

iv. Modulating Root Development

Methods for modulating root development in a plant are provided. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development or radial expansion.

Methods for modulating root development in a plant are provided. The methods comprise modulating the level and/or activity of the ARGOS polypeptide in the plant. In one method, an ARGOS sequence of the invention is provided to the plant. In another method, the ARGOS nucleotide sequence is provided by introducing into the plant a polynucleotide comprising an ARGOS nucleotide sequence of the invention, expressing the ARGOS sequence and thereby modifying root development. In still other methods, the ARGOS nucleotide construct introduced into the plant is stably incorporated into the genome of the plant.

In other methods, root development is modulated by altering the level or activity of the ARGOS polypeptide in the plant. An increase in ARGOS activity can result in at least one or more of the following alterations to root development, including, but not limited to, larger root meristems, increased in root growth, enhanced radial expansion, an enhanced vasculature system, increased root branching, more adventitious roots and/or an increase in fresh root weight when compared to a control plant.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc.

Methods of measuring such developmental alterations in the root system are known in the art. See, for example, US Patent Application Publication Number 2003/0074698 and Werner, et al., (2001) *PNAS* 18:10487-10492, both of which are herein incorporated by reference.

As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Stimulating root growth and increasing root mass by increasing the activity and/or level of the ARGOS polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse (environmental) conditions. This trait relates to the size, depth and morphology of the root system. In addition, stimulating root growth and increasing root mass by increasing the level and/or activity of the ARGOS polypeptide also finds use in promoting in vitro propagation of explants.

Furthermore, higher root biomass production due to an increased level and/or activity of ARGOS activity has a direct effect on the yield and an indirect effect of production of compounds produced by root cells or transgenic root cells or cell cultures of said transgenic root cells. One example of an interesting compound produced in root cultures is shikonin, the yield of which can be advantageously enhanced by said methods.

Accordingly, the present invention further provides plants having modulated root development when compared to the root development of a control plant. In some embodiments, the plant of the invention has an increased level/activity of the ARGOS polypeptide of the invention and has enhanced root growth and/or root biomass. In other embodiments, such plants have stably incorporated into their genome a nucleic acid molecule comprising a ARGOS nucleotide sequence of the invention operably linked to a promoter that drives expression in the plant cell.

v. Modulating Shoot and Leaf Development

Methods are also provided for modulating shoot and leaf development in a plant. By "modulating shoot and/or leaf development" is intended any alteration in the development of the plant shoot and/or leaf. Such alterations in shoot and/or leaf development include, but are not limited to, alterations in shoot meristem development, in leaf number, leaf size, leaf and stem vasculature, internode length and leaf senescence. As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) PNAS 98:10487-10492 and US Patent Application Publication Number 2003/0074698, each of which is herein incorporated by reference.

The method for modulating shoot and/or leaf development in a plant comprises modulating the activity and/or level of an ARGOS polypeptide of the invention. In one embodiment, an ARGOS sequence of the invention is provided. In other embodiments, the ARGOS nucleotide sequence can be provided by introducing into the plant a polynucleotide comprising an ARGOS nucleotide sequence of the invention, expressing the ARGOS sequence and thereby modifying shoot and/or leaf development. In other embodiments, the ARGOS nucleotide construct introduced into the plant is stably incorporated into the genome of the plant.

In specific embodiments, shoot or leaf development is modulated by decreasing the level and/or activity of the ARGOS polypeptide in the plant. An decrease in ARGOS activity can result in at least one or more of the following alterations in shoot and/or leaf development, including, but not limited to, reduced leaf number, reduced leaf surface, reduced vascular, shorter internodes and stunted growth and retarded leaf senescence, when compared to a control plant.

As discussed above, one of skill will recognize the appropriate promoter to use to modulate shoot and leaf development of the plant. Exemplary promoters for this embodiment include constitutive promoters, shoot-preferred promoters, shoot meristem-preferred promoters and leaf-preferred promoters. Exemplary promoters have been disclosed elsewhere herein.

Decreasing ARGOS activity and/or level in a plant results in shorter internodes and stunted growth. Thus, the methods of the invention find use in producing dwarf plants. In addition, as discussed above, modulation of ARGOS activity in the plant modulates both root and shoot growth. Thus, the present invention further provides methods for altering the root/shoot ratio. Shoot or leaf development can further be modulated by decreasing the level and/or activity of the ARGOS polypeptide in the plant.

Accordingly, the present invention further provides plants having modulated shoot and/or leaf development when compared to a control plant. In some embodiments, the plant of the invention has an increased level/activity of the ARGOS polypeptide of the invention, altering the shoot and/or leaf development. Such alterations include, but are not limited to, increased leaf number, increased leaf surface, increased vascularity, longer internodes and increased plant stature, as well as alterations in leaf senescence, as compared to a control plant. In other embodiments, the plant of the invention has a decreased level/activity of the ARGOS polypeptide of the invention.

vi Modulating Reproductive Tissue Development

Methods for modulating reproductive tissue development are provided. In one embodiment, methods are provided to modulate floral development in a plant. By "modulating floral development" is intended any alteration in a structure of a plant's reproductive tissue as compared to a control plant in which the activity or level of the ARGOS polypeptide has not been modulated. "Modulating floral development" further includes any alteration in the timing of the development of a plant's reproductive tissue (i.e., a delayed or an accelerated timing of floral development) when compared to a control plant in which the activity or level of the ARGOS polypeptide has not been modulated. Macroscopic alterations may include changes in size, shape, number, or location of reproductive organs, the developmental time period that these structures form, or the ability to maintain or proceed through the flowering process in times of environmental stress. Microscopic alterations may include changes to the types or shapes of cells that make up the reproductive organs.

The method for modulating floral development in a plant comprises modulating ARGOS activity in a plant. In one method, an ARGOS sequence of the invention is provided. An ARGOS nucleotide sequence can be provided by introducing into the plant a polynucleotide comprising an ARGOS nucleotide sequence of the invention, expressing the ARGOS sequence and thereby modifying floral development. In other embodiments, the ARGOS nucleotide construct introduced into the plant is stably incorporated into the genome of the plant.

In specific methods, floral development is modulated by decreasing the level or activity of the ARGOS polypeptide in the plant. A decrease in ARGOS activity can result in at least one or more of the following alterations in floral development, including, but not limited to, retarded flowering, reduced number of flowers, partial male sterility and reduced seed set, when compared to a control plant. Inducing delayed flowering or inhibiting flowering can be used to enhance yield in forage crops such as alfalfa. Methods for measuring such developmental alterations in floral development are known in the art. See, for example, Mouradov, et al., (2002) *The Plant Cell* S111-S130, herein incorporated by reference.

As discussed above, one of skill will recognize the appropriate promoter to use to modulate floral development of the plant. Exemplary promoters for this embodiment include constitutive promoters, inducible promoters, shoot-preferred promoters and inflorescence-preferred promoters.

In other methods, floral development is modulated by increasing the level and/or activity of the ARGOS sequence of the invention. Such methods can comprise introducing an ARGOS nucleotide sequence into the plant and increasing the activity of the ARGOS polypeptide. In other methods, the ARGOS nucleotide construct introduced into the plant is stably incorporated into the genome of the plant. Increasing expression of the ARGOS sequence of the invention can modulate floral development during periods of stress. Such methods are described elsewhere herein. Accordingly, the present invention further provides plants having modulated floral development when compared to the floral development of a control plant. Compositions include plants having an increased level/activity of the ARGOS polypeptide of the invention and having an altered floral development. Compositions also include plants having an increased level/activity of the ARGOS polypeptide of the invention wherein the plant maintains or proceeds through the flowering process in times of stress.

Methods are also provided for the use of the ARGOS sequences of the invention to increase seed size and/or weight. The method comprises increasing the activity of the ARGOS sequences in a plant or plant part, such as the seed. An increase in seed size and/or weight comprises an increased size or weight of the seed and/or an increase in the size or weight of one or more seed part including, for example, the embryo, endosperm, seed coat, aleurone or cotyledon.

As discussed above, one of skill will recognize the appropriate promoter to use to increase seed size and/or seed weight. Exemplary promoters of this embodiment include constitutive promoters, inducible promoters, seed-preferred promoters, embryo-preferred promoters and endosperm-preferred promoters.

The method for decreasing seed size and/or seed weight in a plant comprises decreasing ARGOS activity in the plant. In one embodiment, the ARGOS nucleotide sequence can be provided by introducing into the plant a polynucleotide comprising a ARGOS nucleotide sequence of the invention, expressing the ARGOS sequence and thereby decreasing seed weight and/or size. In other embodiments, the ARGOS nucleotide construct introduced into the plant is stably incorporated into the genome of the plant.

It is further recognized that increasing seed size and/or weight can also be accompanied by an increase in the speed of growth of seedlings or an increase in early vigor. As used herein, the term "early vigor" refers to the ability of a plant to grow rapidly during early development, and relates to the successful establishment, after germination, of a well-developed root system and a well-developed photosynthetic apparatus. In addition, an increase in seed size and/or weight can also result in an increase in plant yield when compared to a control.

Accordingly, the present invention further provides plants having an increased seed weight and/or seed size when compared to a control plant. In other embodiments, plants having an increased vigor and plant yield are also provided. In some embodiments, the plant of the invention has an increased level/activity of the ARGOS polypeptide of the invention and has an increased seed weight and/or seed size. In other embodiments, such plants have stably incorporated into their genome a nucleic acid molecule comprising a ARGOS nucleotide sequence of the invention operably linked to a promoter that drives expression in the plant cell.

vii. Method of Use for ARGOS Promoter Polynucleotides

The polynucleotides comprising the ARGOS promoters disclosed in the present invention, as well as variants and fragments thereof, are useful in the genetic manipulation of any host cell, preferably plant cell, when assembled with a DNA construct such that the promoter sequence is operably linked to a nucleotide sequence comprising a polynucleotide of interest. In this manner, the ARGOS promoter polynucleotides of the invention are provided in expression cassettes along with a polynucleotide sequence of interest for expression in the host cell of interest. As discussed in Example 2 below, the ARGOS promoter sequences of the invention are expressed in a variety of tissues and thus the promoter sequences can find use in regulating the temporal and/or the spatial expression of polynucleotides of interest.

Synthetic hybrid promoter regions are known in the art. Such regions comprise upstream promoter elements of one polynucleotide operably linked to the promoter element of another polynucleotide. In an embodiment of the invention, heterologous sequence expression is controlled by a synthetic hybrid promoter comprising the ARGOS promoter sequences of the invention, or a variant or fragment thereof, operably linked to upstream promoter element(s) from a heterologous promoter. Upstream promoter elements that are involved in the plant defense system have been identified and may be used to generate a synthetic promoter. See, for example, Rushton, et al., (1998) *Curr. Opin. Plant Biol.* 1:311-315. Alternatively, a synthetic ARGOS promoter sequence may comprise duplications of the upstream promoter elements found within the ARGOS promoter sequences.

It is recognized that the promoter sequence of the invention may be used with its native ARGOS coding sequences. A DNA construct comprising the ARGOS promoter operably linked with its native ARGOS gene may be used to transform any plant of interest to bring about a desired phenotypic change, such as modulating cell nubmer, modulating root, shoot, leaf, floral and embryo development, stress tolerance and any other phenotype described elsewhere herein.

The promoter nucleotide sequences and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases and those involved in housekeeping, such as heat shock proteins. More specific categories of transgenes, for example, include genes encoding important traits for agronomics, insect resistance, disease resistance, herbicide resistance, sterility, grain characteristics and commercial products. Genes of interest include, generally, those involved in oil, starch, carbohydrate or nutrient metabolism as well as those affecting kernel size, sucrose loading, and the like.

In certain embodiments the nucleic acid sequences of the present invention can be used in combination ("stacked") with other polynucleotide sequences of interest in order to create plants with a desired phenotype. The combinations generated can include multiple copies of any one or more of the polynucleotides of interest. The polynucleotides of the present invention may be stacked with any gene or combination of genes to produce plants with a variety of desired trait combinations, including but not limited to traits desirable for animal feed such as high oil genes (e.g., U.S. Pat. No. 6,232,529); balanced amino acids (e.g., hordothionins (U.S. Pat. Nos. 5,990,389; 5,885,801; 5,885,802 and 5,703,409); barley high lysine (Williamson, et al., (1987) *Eur. J. Biochem.* 165: 99-106 and WO 98/20122) and high methionine proteins (Pedersen, et al., (1986) *J. Biol. Chem.* 261:6279; Kirihara, et al., (1988) *Gene* 71:359 and Musumura, et al., (1989) *Plant Mol. Biol.* 12:123); increased digestibility (e.g., modified storage proteins (U.S. patent application Ser. No. 10/053,410, filed Nov. 7, 2001) and thioredoxins (U.S. patent application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene) and glyphosate resistance (EPSPS gene)) and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)) and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see, U.S. Pat. No. 5,583,210), stalk strength, flowering time or transformation technology traits such as cell cycle regulation or gene targeting (e.g., WO 99/61619; WO 00/17364; WO 99/25821), the disclosures of which are herein incorporated by reference.

In one embodiment, sequences of interest improve plant growth and/or crop yields. For example, sequences of interest include agronomically important genes that result in improved primary or lateral root systems. Such genes include, but are not limited to, nutrient/water transporters and growth induces. Examples of such genes, include but are not limited to, maize plasma membrane $H^+$-ATPase (MHA2) (Frias, et al., (1996) *Plant Cell* 8:1533-44); AKT1, a component of the potassium uptake apparatus in *Arabidopsis*, (Spalding, et al., (1999) *J Gen Physiol* 113:909-18); RML genes which activate cell division cycle in the root apical cells (Cheng, et al., (1995) *Plant Physiol* 108:881); maize glutamine synthetase genes (Sukanya, et al., (1994) *Plant Mol Biol* 26:1935-46) and hemoglobin (Duff, et al., (1997) *J. Biol. Chem.* 27:16749-16752, Arredondo-Peter, et al., (1997) *Plant Physiol.* 115: 1259-1266; Arredondo-Peter, et al., (1997) *Plant Physiol* 114:493-500 and references sited therein). The sequence of interest may also be useful in expressing antisense nucleotide sequences of genes that that negatively affects root development.

Additional, agronomically important traits such as oil, starch and protein content can be genetically altered in addition to using traditional breeding methods. Modifications include increasing content of oleic acid, saturated and unsaturated oils, increasing levels of lysine and sulfur, providing essential amino acids and also modification of starch. Hordothionin protein modifications are described in U.S. Pat. Nos. 5,703,049, 5,885,801, 5,885,802 and 5,990,389, herein incorporated by reference. Another example is lysine and/or sulfur rich seed protein encoded by the soybean 2S albumin described in U.S. Pat. No. 5,850,016 and the chymotrypsin inhibitor from barley, described in Williamson, et al., (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. patent application Ser. No. 08/740,682, filed Nov. 1, 1996, and WO 98/20133, the disclosures of which are herein incorporated by reference. Other proteins include methionine-rich plant proteins such as from sunflower seed (Lilley, et al., (1989) *Proceedings of the World Congress on Vegetable Protein Utilization in Human Foods and Animal Feedstuffs*, ed. Applewhite (American Oil Chemists Society, Champaign, Ill.), pp. 497-502, herein incorporated by reference); corn (Pedersen, et al., (1986) *J. Biol. Chem.* 261:6279; Kirihara, et al., (1988) *Gene* 71:359, both of which are herein incorporated by reference) and rice (Musumura, et al., (1989) *Plant Mol. Biol.* 12:123, herein incorporated by reference). Other agronomically important genes encode latex, Floury 2, growth factors, seed storage factors and transcription factors.

Insect resistance genes may encode resistance to pests that have great yield drag such as rootworm, cutworm, European Corn Borer and the like. Such genes include, for example, Bacillus thuringiensis toxic protein genes (U.S. Pat. Nos. 5,366,892; 5,747,450; 5,736,514; 5,723,756; 5,593,881 and Geiser, et al., (1986) Gene 48:109), and the like.

Genes encoding disease resistance traits include detoxification genes, such as against fumonosin (U.S. Pat. No. 5,792, 931); avirulence (avr) and disease resistance (R) genes (Jones, et al., (1994) Science 266:789; Martin, et al., (1993) Science 262:1432; and Mindrinos, et al., (1994) Cell 78:1089), and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids and levels of cellulose. In corn, modified hordothionin proteins are described in U.S. Pat. Nos. 5,703,049, 5,885,801, 5,885,802 and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as 13-Ketothiolase, PHBase (polyhydroxyburyrate synthase), and acetoacetyl-CoA reductase (see, Schubert, et al., (1988) J. Bacteriol. 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones and the like. The level of proteins, particularly modified proteins having improved amino acid distribution to improve the nutrient value of the plant, can be increased. This is achieved by the expression of such proteins having enhanced amino acid content.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

Example 1

Isolation of ARGOS Sequences

A routine for identifying all members of a gene family was employed to search for the ARGOS genes of interest. A diverse set of all the known members of the gene family as protein sequences was prepared. This data includes sequences from other species. These species are searched against a proprietary maize sequence dataset and a nonredundant set of overlapping hits is identified. Separately, one takes the nucleotide sequences of any genes of interest in hand and searches against the database and a nonredundant set of all overlapping hits are retrieved. The set of protein hits are then compared to the nucleotide hits. If the gene family is complete, all of the protein hits are contained within the nucleotide hits. The ARGOS family of genes consists of 3 Arabidopsis genes, 8 rice genes, 9 maize genes, 9 sorghum genes and 5 soybean genes. A dendrogram representation of the interrelationship of the proteins encoded by these genes is provided as FIG. 1.

Example 2

ARGOS Sequence Analysis

Figure 2C:
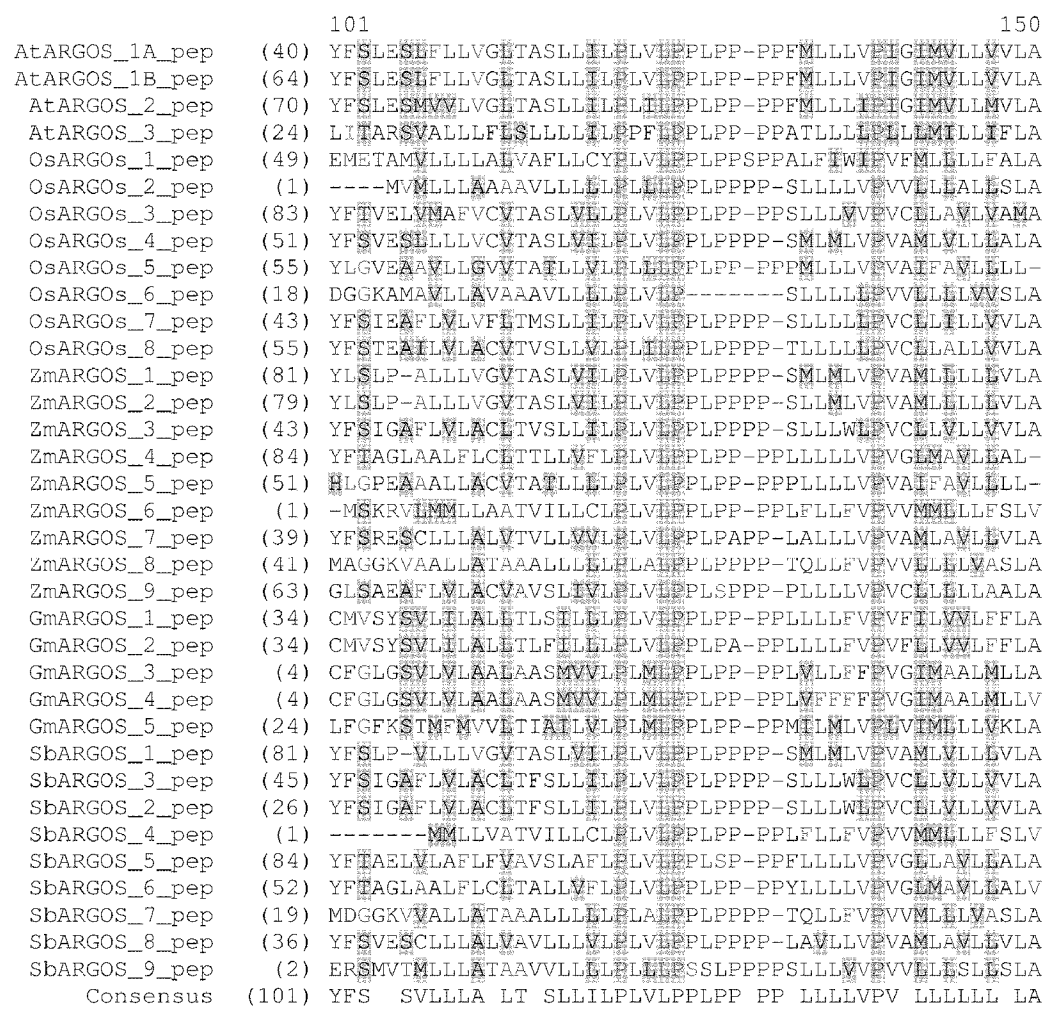

The ZmARGOS polypeptides of the current invention have common characteristics with ARGOS genes in a variety of plant species. The relationship between the genes of the multiple plant species is shown in an alignment, see, FIG. 2. FIG. 3 contains ZmARGOS 1, 2, 3 and AtARGOS 1 (SEQ ID NOS: 2, 4, 6 and 26). The proteins encoded by the ARGOS genes have a well-conserved proline rich region near the C-terminus. The N-termini are more divergent. The proteins are relatively short, averaging 110 amino acids.

Example 3

Transformation and Regeneration of Transgenic Plants

Immature maize embryos from greenhouse donor plants are bombarded with a plasmid containing the ZmARGOS sequence operably linked to the drought-inducible promoter RAB17 promoter (Vilardell, et al., (1990) Plant Mol Biol 14:423-432) and the selectable marker gene PAT, which confers resistance to the herbicide Bialaphos. Alternatively, the selectable marker gene is provided on a separate plasmid. Transformation is performed as follows. Media recipes follow below.

Preparation of Target Tissue:

The ears are husked and surface sterilized in 30% CLOROX bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA:

A plasmid vector comprising the ARGOS sequence operably linked to an ubiquitin promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

Particle Gun Treatment:

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment:

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for increased drought tolerance. Assays to measure improved drought tolerance are routine in the art and include, for example, increased kernel-earring capacity yields under drought conditions when compared to control maize plants under identical environmental conditions. Alternatively, the transformed plants can be monitored for a modulation in meristem development (i.e., a decrease in spikelet formation on the ear). See, for example, Bruce, et al., (2002) *Journal of Experimental Botany* 53:1-13.

Bombardment and Culture Media:

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCI, 120.0 g/l sucrose, 1.0 mg/l 2,4-D, and 2.88 g/l L-proline (brought to volume with D-I $H_2O$ following adjustment to pH 5.8 with KOH); 2.0 g/l GELRITE (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCI, 30.0 g/l sucrose, and 2.0 mg/l 2,4-D (brought to volume with D-I $H_2O$ following adjustment to pH 5.8 with KOH); 3.0 g/l GELRITE (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l GELRITE (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l BACTO-agar (added after bringing to volume with polished D-I $H_2O$), sterilized and cooled to 60° C.

Example 4

Agrobacterium-Mediated Transformation

For *Agrobacterium*-mediated transformation of maize with an antisense sequence of the ZmARGOS sequence of the present invention, preferably the method of Zhao is employed (U.S. Pat. No. 5,981,840 and PCT Patent Publication Number WO 98/32326, the contents of which are hereby incorporated by reference). Briefly, immature embryos are isolated from maize and the embryos contacted with a suspension of *Agrobacterium*, where the bacteria are capable of transferring the ARGOS sequence to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants. Plants are monitored and scored for a modulation in meristem development. For instance, alterations of size and appearance of the shoot and floral meristems and/or increased yields of leaves, flowers and/or fruits.

Example 5

Over Expression of ZmARGOS Affects Plant Size and Organ Size

The function of the ZmARGOS gene was tested by using transgenic plants expressing the Ubi-ZmARGOS transgene. Transgene expression was confirmed by using transgene-specific primer RT-PCR (SEQ ID NO: 38 for ARGOS and SEQ ID NO: 39 for PIN). T1 plants from nine single-copy events were evaluated in the field. Transgenic plants showed positive growth enhancements in several aspects.

Vegetative Growth and Biomass Accumulation:

Compared to the non transgenic sibs, the transgenic plants (in T1 generation) showed an average of 4% increase in plant height across all 9 events and up to 12% in the highest event. The stem of the transgenic plants was thicker than the non transgenic siblings as measured by stem diameter values with an average of 9% to 22% increase among the nine events. The increase of the plant height and the stem thickness resulted in a larger plant stature and biomass for the transgenic plants. Estimated biomass accumulation showed an increase of 30% on average and up to 57% in transgenic positive lines compared to the negative siblings.

ZmARGOS was found to impact plant growth mainly through accelerating the growth rate but not extending the growth period. The enhanced growth, i.e., increased plant size and biomass accumulation, appears to be largely due to an accelerated growth rate and not due to an extended period of growth because the transgenic plants were not delayed in flowering based on the silking and anthesis dates. In fact, the transgenic plants flowered earlier than the non-transgenic siblings. On average across the events, the days to flowering was shortened to between 30 heat units (1-1.5 days), and 69 heat units (2-2.5 days). Therefore, overexpressing of the ZmARGOS gene accelerated the growth rate of the plant. Accelerated growth rate appears to be associated with an increased cell proliferation rate.

The enhanced vegetative growth, biomass accumulation in transgenics and accelerated growth rate were further tested with extensive field experiments in both hybrid and inbred backgrounds at advanced generation (T3). Transgenic plants reproducibly showed increased plant height up to 18%, stem diameter up to 10%, stalk dry mass up to 15%, increased leaf area up to 14%, total plant dry mass up to 25%. Earlier flowering observed in T1 generation was again observed in T3 generation.

Reproductive Growth and Grain Yield:

Overexpression of the ZmARGOS 1 gene also enhanced the reproductive organ growth. T1 Transgenic plants showed increased ear length, about 10% on the average of nine events, and up to 14% for the highest event. Total kernel weight per ear increased 13% on average and up to 70% for one event. The increase in total kernel weight appears to be attributed to the increased kernel numbers per ear and kernel size. The average of the nine events showed that the kernel number per ear increased 8%, and up to 50% in the highest event. The 100-kernel weight increased 5% on average, and up to 13% for the highest event. The positive change in kernel and ear characteristics is associated with grain yield increase.

The enhanced reproductive growth and grain yield of transgenics was again confirmed in extensive field experiments at the advanced generation (T3). The enhancement was observed in both inbred and hybrid backgrounds. As compared to the non-transgenic sibs as controls, the transgenic plants showed a significantly increase in primary ear dry mass up to 60%, secondary ear dry mass up to 4.7 folds, tassel dry mass up to 25% and husk dry mass up to 40%. The transgenics showed up to 13% increase in kernel number per ear, and up to 13% grain yield increase.

Transgenic plants also showed reduced ASI, up to 40 heat units, reduced barrenness up to 50% and reduced number of aborted kernels up to 64%. The reduction is more when the plants were grown at a high plant density stressed condition. A reduced measurement of these parameters is often related to tolerance to biotic stress.

In addition, transgene expression level is significantly correlated with the ear dry mass.

Example 6

Soybean Embryo Transformation

Soybean embryos are bombarded with a plasmid containing an ARGOS sequence operably linked to an ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) *Nature* (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium tumefaciens*. The expression cassette comprising an ARGOS sense sequence operably linked to the ubiquitin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Sunflower Meristem Tissue Transformation

Sunflower meristem tissues are transformed with an expression cassette containing an ARGOS sequence operably linked to a ubiquitin promoter as follows (see also, European Patent Number EP 0 486233, herein incorporated by reference, and Malone-Schoneberg, et al., (1994) *Plant Science* 103:199-207). Mature sunflower seed (*Helianthus annuus* L.) are dehulled using a single wheat-head thresher. Seeds are surface sterilized for 30 minutes in a 20% CLOROX bleach solution with the addition of two drops of TWEEN 20 per 50 ml of solution. The seeds are rinsed twice with sterile distilled water.

Split embryonic axis explants are prepared by a modification of procedures described by Schrammeijer, et al., (Schrammeijer, et al., (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) Physiol. Plant., 15:473-497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l PHYTAGAR.

The explants are subjected to microprojectile bombardment prior to *Agrobacterium* treatment (Bidney, et al., (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the ARGOS gene operably linked to the ubiquitin promoter is introduced into Agrobacterium strain EHA105 via freeze-thawing as described by Holsters, et al., (1978) *Mol. Gen. Genet.* 163:181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l BACTOpeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The Agrobacterium cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for a modulation in meristem development (i.e., an alteration of size and appearance of shoot and floral meristems).

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% GELRITE, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by ARGOS activity analysis of leaf extracts while transgenic seeds harvested from NPTII-positive $T_0$ plants are identified by ARGOS activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% CLOROX bleach solution with the addition of two to three drops of TWEEN 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% PHYTAGAR at pH 5.6) for 24 hours under the dark. The primary leaves are removed to expose the apical meristem, around 40 explants are placed with the apical dome facing upward in a 2 cm circle in the center of 374M (GBA medium with 1.2% PHYTAGAR), and then cultured on the medium for 24 hours in the dark.

Approximately 18.8 mg of 1.8 μm tungsten particles are resuspended in 150 μl absolute ethanol. After sonication, 8 μl of it is dropped on the center of the surface of macrocarrier. Each plate is bombarded twice with 650 psi rupture discs in the first shelf at 26 mm of Hg helium gun vacuum.

The plasmid of interest is introduced into Agrobacterium tumefaciens strain EHA105 via freeze thawing as described previously. The pellet of overnight-grown bacteria at 28° C. in a liquid YEP medium (10 g/l yeast extract, 10 g/l BACTOpeptone, and 5 g/l NaCl, pH 7.0) in the presence of 50 μg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374C medium are screened for a modulation in meristem development (i.e., an alteration of size and appearance of shoot and floral meristems). After positive (i.e., a change in ARGOS expression) explants are identified, those shoots that fail to exhibit an alteration in ARGOS activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for altered ARGOS expression are grafted to Pioneer hybrid 6440 in vitro-grown sunflower seedling rootstock. The rootstocks are prepared in the following manner. Seeds are dehulled and surface-sterilized for 20 minutes in a 20% CLOROX bleach solution with the addition of two to three drops of TWEEN 20 per 100 ml of solution, and are rinsed three times with distilled water. The sterilized seeds are germinated on the filter moistened with water for three days, then they are transferred into 48 medium (half-strength MS salt, 0.5% sucrose, 0.3% GELRITE pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

Example 8

Variants of ARGOS Sequences

A. Variant Nucleotide Sequences of ARGOS that do not Alter the Encoded Amino Acid Sequence The ARGOS nucleotide sequences are used to generate variant nucleotide sequences having the nucleotide sequence of the open reading frame with about 70%, 75%, 80%, 85%, 90% and 95% nucleotide sequence identity when compared to the starting unaltered ORF nucleotide sequence of the corresponding SEQ ID NO. These functional variants are generated using a standard codon table. While the nucleotide sequence of the variants are altered, the amino acid sequence encoded by the open reading frames do not change.

B. Variant Amino Acid Sequences of ARGOS Polypeptides

Variant amino acid sequences of the ARGOS polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using the protein alignment set forth in FIG. 2, an appropriate amino acid can be changed. Once the targeted amino acid is identified, the procedure outlined in the following section C is followed. Variants having about 70%, 75%, 80%, 85%, 90% and 95% nucleic acid sequence identity are generated using this method.

C. Additional Variant Amino Acid Sequences of ARGOS Polypeptides

In this example, artificial protein sequences are created having 80%, 85%, 90% and 95% identity relative to the reference protein sequence. This latter effort requires identifying conserved and variable regions from the alignment set forth in FIG. 2 and then the judicious application of an amino acid substitutions table. These parts will be discussed in more detail below.

Largely, the determination of which amino acid sequences are altered is made based on the conserved regions among ARGOS protein or among the other ARGOS polypeptides. Based on the sequence alignment, the various regions of the ARGOS polypeptide that can likely be altered are represented in lower case letters, while the conserved regions are represented by capital letters. It is recognized that conservative substitutions can be made in the conserved regions below without altering function. In addition, one of skill will understand that functional variants of the ARGOS sequence of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 3.

TABLE 3

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of the ARGOS polypeptides are generating having about 80%, 85%, 90% and 95% amino acid identity to the starting unaltered ORF nucleotide sequence of SEQ ID NOS: 1, 3, 5 and 40-71.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. A method of modulating organ size in plants, comprising:
   a. introducing into a plant cell a recombinant expression cassette comprising a polynucleotide encoding the polypeptide of SEQ ID NO: 11, the polynucleotide operably linked to a promoter; and
   b. culturing the plant under plant cell growing conditions; wherein the organ size in said plant cell is modulated.

2. The method of claim 1, wherein the plant cell is from a plant selected from the group consisting of: maize, soybean, sunflower, sorghum, canola, wheat, alfalfa, cotton, rice, barley, millet, peanut and cocoa.

3. A method of modulating the whole plant size or organ size in a plant, comprising:
   a. introducing into a plant cell a recombinant expression cassette comprising a polynucleotide encoding the polypeptide of SEQ ID NO: 11, the polynucleotide operably linked to a promoter;
   b. culturing the plant cell under plant cell growing conditions; and
   c. regenerating a plant form said plant cell; wherein the whole plant size or organ size in said plant is modulated.

4. The method of claim 3, wherein the plant is selected from the group consisting of: maize, soybean, sorghum, canola, wheat, alfalfa, cotton, rice, barley, millet, peanut, and cocoa.

* * * * *

SEQUENCE LISTING

```
<160> NUMBER OF SEQ ID NOS: 71

<210> SEQ ID NO 1
<211> LENGTH: 879
<212> TYPE: DNA
<213> ORGANISM: Zea mays

<400> SEQUENCE: 1
tttttagcta gctagatctg gcctgattcg ccgatcgagc ggtggtgaga cggagtgctt      60
cagctcaaag actgctagtg gtaggctggt agctagctgt gtgcctgtgt gcagtgtgca     120
ctgccactgc atgcgcggcg ccttggactt aagacggcag cacacgcacg cgaggaggcg     180
tcggctgaag cgagcgctcc ggcggctccg cttcgctcat caggttcttg agccccggaa     240
acgatgagca cgacccggcc ggaggacacc cagcaactga tcaacagtgc cgccgctagc     300
cccaaccgca gcgcaccgtc cgccgcgccc agcgatatgg agaggggcag cggaaccgcc     360
gcgtcctcgt cgcgcgcttc gacgacgtct cactcccacc agagggccac ccacagggtg     420
gtggaggagg aggaggagga ggagcctagt agcagccgtg gcggcggcag cctctgctcc     480
gggtacctgt cgctcccggc tctgctgctc gtcggcgtca ccgcgtcgct ggtgatcctc     540
ccgctcgtcc tgcccccgct gccgccgccg ccgtcgatgc tgatgctggt ccccgtggca     600
atgctgctcc tgctgctcgt gctggcgttc atgcccacgt cgtccaccgg cggccgcggt     660
ggaaccggac cgacctacat gtagataatc acatcggttt tttttttcct ttctttctct     720
tgtcgtcctt tcgtttggat tttgtgacag agggaggtct tgcgatggat cagttagtcc     780
tcagcttctg ctcttctcga tcgtacgatg tctctgttcg gctaattaat ttgcataggg     840
gtatatatat gctgcctaga tcttaaaagt atctcgtgc                           879

<210> SEQ ID NO 2
<211> LENGTH: 146
<212> TYPE: PRT
<213> ORGANISM: Zea mays

<400> SEQUENCE: 2

Met Ser Thr Thr Arg Pro Glu Asp Thr Gln Gln Leu Ile Asn Ser Ala
 1               5                  10                  15

Ala Ala Ser Pro Asn Arg Ser Ala Pro Ser Ala Ala Pro Ser Asp Met
            20                  25                  30

Glu Arg Gly Ser Gly Thr Ala Ala Ser Ser Ser Arg Ala Ser Thr Thr
        35                  40                  45

Ser His Ser His Gln Arg Ala Thr His Arg Val Val Glu Glu Glu Glu
    50                  55                  60

Glu Glu Glu Pro Ser Ser Ser Arg Gly Gly Gly Ser Leu Cys Ser Gly
65                  70                  75                  80
```

```
Tyr Leu Ser Leu Pro Ala Leu Leu Val Gly Val Thr Ala Ser Leu
                85                  90                  95

Val Ile Leu Pro Leu Val Leu Pro Leu Pro Pro Pro Ser Met
            100                 105                 110

Leu Met Leu Val Pro Val Ala Met Leu Leu Leu Leu Val Leu Ala
        115                 120                 125

Phe Met Pro Thr Ser Ser Thr Gly Gly Arg Gly Gly Thr Gly Pro Thr
        130                 135                 140

Tyr Met
145

<210> SEQ ID NO 3
<211> LENGTH: 936
<212> TYPE: DNA
<213> ORGANISM: Zea mays

<400> SEQUENCE: 3
caacgtccaa cccctcttgt ctctcgtcta cctctcttct gccctctgc gtccgtgtct      60 ccctcgtcgt cgctgcgtga ggttgacgac gaccagtcac aggatctgtt cgttcctcat    120
gcgacccagc tagctaaaac tggcatgcat ggacatgcta cgctgctgcg tcaatccatc    180
tcaccagcag tgctagctag ctagatctgg cctgattcgc cgatcgagcg gtcgccggtc    240
agagactcag agttcatgag acggagtgct tcagctcaaa gactgctagt ggtagctagg    300
tagctgcgtg cactgcatgc gcggcgcctt ggacttgaag aaaccgagcg ctccgatagt    360
ccgatccgga aacgatgagt gccgggccgg aggacaccca gcagctgatc aacagtgccg    420
ccgctagccc caaccgcagc gcaccgtccg ccgcgcccag cgatatggag aggggcagcg    480
gaaccgccgc gtcctcgtcg cgcgcttcga cgacgtccca ctcccaccag agggccaccc    540
acagggtggt ggaggaggag gaggaggagc ctagtagcag ccgtggcgcc ggcagcctct    600
gctccgggta cctgtcgctt ccggctctgc tgctcgtcgg cgtcaccgcg tcgctggtga    660
tcctcccgct cgtcctgccc ccgctgccgc cgccgccgtc gttgctgatg ctggtccccg    720
tggcaatgct gctcctgctg ctcgtgctgg cgttcatgcc cacgtcgtcc accggcggcc    780
gcggtggaac cggaccgacc tacatgtaga taatcacatc ggttttttt tttttccttt    840 ctttctcttg tcgtcctttc gtttggattt tgtgacagag ggaggtcttg cgatggatca    900
gttagtcctc aaaaaaaaaa aaaaaaaaaa aaaaaa                              936

<210> SEQ ID NO 4
<211> LENGTH: 144
<212> TYPE: PRT
<213> ORGANISM: Zea mays

<400> SEQUENCE: 4

Met Ser Ala Gly Pro Glu Asp Thr Gln Gln Leu Ile Asn Ser Ala Ala
1               5                   10                  15

Ala Ser Pro Asn Arg Ser Ala Pro Ala Ala Pro Ser Asp Met Glu
                20                  25                  30

Arg Gly Ser Gly Thr Ala Ala Ser Ser Arg Ala Ser Thr Thr Ser
            35                  40                  45

His Ser His Gln Arg Ala Thr His Arg Val Val Glu Glu Glu Glu
        50                  55                  60

Glu Pro Ser Ser Arg Gly Ala Gly Ser Leu Cys Ser Gly Tyr Leu
65                  70                  75                  80

Ser Leu Pro Ala Leu Leu Leu Val Gly Val Thr Ala Ser Leu Val Ile
                85                  90                  95
```

```
Leu Pro Leu Val Leu Pro Pro Leu Pro Pro Pro Ser Leu Leu Met
            100                 105                 110
Leu Val Pro Val Ala Met Leu Leu Leu Leu Val Leu Ala Phe Met
        115                 120                 125
Pro Thr Ser Ser Thr Gly Gly Arg Gly Gly Thr Gly Pro Thr Tyr Met
    130                 135                 140
```

<210> SEQ ID NO 5
<211> LENGTH: 1067
<212> TYPE: DNA
<213> ORGANISM: Zea mays

<400> SEQUENCE: 5

```
ctccatcctt cccccgggga gcaggagctg cagccaggag tcgagtcggc gtcgtcacgg      60
gagatatcag cttcgctatc accggatccc ccctctgctc cctccgcacc tcccatctgc     120
gctctctgtt ttcttccgcg caccccggct gttggtgtcc cgtccggcgg cgttgctggt     180
ggctgaatcc gagcctttga ggggtctccc gccgccgccg ctcttgagat ctctttattg     240
atctggaggg attaaagagg gattcttgcc ttcctactgg agcaagagaa aggggagaac     300
gtgtttcttc aggcgtggtt gaacagtgag gaccggagaa caatgcgagg ttcgggattt     360
aagatgttct ggctttaggg gccgttcttc tgaagcaggg gacgggcgat tcgaccaccg     420
gagctcagat ctgattacaa aacgttcaga aaacacaagg cgttctcaca ccgcctttca     480
cttcttgctt actttggcaa ccactcactg cgactggtct ccactccac ctacaccaaa     540
gaacacatgg caagccgatc tagcgcgatg gaaggagggg cggcaataca aggaggaat     600
gccgtgaagc ggcatctgca gcagcgtcag caggaggcgg atttcctcga caagaaggtc     660
atcgcgtcca cctacttcag catcggggcg ttcctcgtgc tcgcctgcct caccgtctcg     720
ctgctgatac tgccgctggt gctgcctccc ctgccgccgc cgccgtcgct gctgctgtgg     780
ctgccggtct gcctgctcgt cttgctggtt gtactggcct tcatgccgac agatgtgcgc     840
agcatggcct cctcttacct gtaaatagat aaataggtct tggccagatt ttctgtgttt     900
tgcagctgca ggattcgtcc taagacgagt catgagtgta atgtgaagca acttctccag     960
ggatagatct caaccaagtt tggtagccat acgaagttat tgactggaat ttagaacata    1020
tagttgtgca caatttcgaa catatcttgt agtggagagc gggccga                  1067
```

<210> SEQ ID NO 6
<211> LENGTH: 105
<212> TYPE: PRT
<213> ORGANISM: Zea mays

<400> SEQUENCE: 6

```
Met Ala Ser Arg Ser Ser Ala Met Glu Gly Gly Ala Ala Ile Gln Arg
  1               5                  10                  15
Arg Asn Ala Val Lys Arg His Leu Gln Gln Arg Gln Gln Glu Ala Asp
             20                  25                  30
Phe Leu Asp Lys Lys Val Ile Ala Ser Thr Tyr Phe Ser Ile Gly Ala
         35                  40                  45
Phe Leu Val Leu Ala Cys Leu Thr Val Ser Leu Leu Ile Leu Pro Leu
     50                  55                  60
Val Leu Pro Pro Leu Pro Pro Pro Ser Leu Leu Trp Leu Pro
 65                  70                  75                  80
Val Cys Leu Leu Val Leu Leu Val Val Leu Ala Phe Met Pro Thr Asp
                 85                  90                  95
```

-continued

Val Arg Ser Met Ala Ser Ser Tyr Leu
            100             105

<210> SEQ ID NO 7
<211> LENGTH: 152
<212> TYPE: PRT
<213> ORGANISM: Zea mays

<400> SEQUENCE: 7

Met Cys Arg Gly Leu Pro Thr Pro Ala Pro Ala Pro Ala Leu Gln Phe
1               5                   10                  15

Gln Ser Gln Asp Cys Ser Arg Gln Gln Arg Gly Thr Thr Gln Ala Pro
            20                  25                  30

Pro Gly Arg Ala Ser Glu Ser Val Arg Ala Cys Met Ala Ala Glu Arg
        35                  40                  45

Lys Ala Ala Ser Arg Pro Ala Ala Cys Gly Arg Met Arg Gly Ala Glu
    50                  55                  60

Gly Ala Lys Pro Arg Gly Arg Gln Ala Lys Ala Arg Ala Pro Pro
65                  70                  75                  80

Gly Gln Gly Tyr Phe Thr Ala Gly Leu Ala Ala Leu Phe Leu Cys Leu
                85                  90                  95

Thr Thr Leu Leu Val Phe Leu Pro Leu Val Leu Pro Pro Leu Pro Pro
            100                 105                 110

Pro Pro Leu Leu Leu Leu Val Pro Val Gly Leu Met Ala Val Leu
        115                 120                 125

Leu Ala Leu Ala Leu Val Pro Ser Asp Gly Arg Ala Ala Ala Ala
    130                 135                 140

Val Ala Ser Ser Ser Cys Val Cys
145                 150

<210> SEQ ID NO 8
<211> LENGTH: 119
<212> TYPE: PRT
<213> ORGANISM: Zea mays

<400> SEQUENCE: 8

Met His Leu Leu Asp Leu Arg Gln Asp Arg Gly Gly Ala Ala Ala
1               5                   10                  15

His Thr Gly Ser Arg Ser Arg Lys Pro Pro Pro Leu Ala Ala Ala
            20                  25                  30

Ala Ala Ala Ala Gly Val Pro Ala Gly Ser Ser Thr Ala Ala Thr
        35                  40                  45

Ala Thr His Leu Gly Pro Glu Ala Ala Ala Leu Leu Ala Cys Val Thr
    50                  55                  60

Ala Thr Leu Leu Leu Pro Leu Val Leu Pro Leu Pro Pro
65                  70                  75                  80

Pro Pro Leu Leu Leu Leu Val Pro Val Ala Ile Phe Ala Val Leu Leu
                85                  90                  95

Leu Leu Val Leu Leu Pro Ser Asp Ala Arg Ala Ala Val Ala Thr Pro
            100                 105                 110

Thr Ser Ser Ala Ser Tyr Leu
        115

<210> SEQ ID NO 9
<211> LENGTH: 64
<212> TYPE: PRT
<213> ORGANISM: Zea mays

<400> SEQUENCE: 9

Met Ser Lys Arg Val Leu Met Met Leu Leu Ala Ala Thr Val Ile Leu
1               5                   10                  15

Leu Cys Leu Pro Leu Val Leu Pro Pro Leu Pro Pro Pro Pro Leu Phe
                20                  25                  30

Leu Leu Phe Val Pro Val Val Met Met Leu Leu Leu Phe Ser Leu Val
            35                  40                  45

Phe Phe Pro Ser Asn His Cys Pro Cys Ser Ser Pro Thr Phe Thr Gln
50                      55                  60

<210> SEQ ID NO 10
<211> LENGTH: 106
<212> TYPE: PRT
<213> ORGANISM: Zea mays

<400> SEQUENCE: 10

Met Pro Ser Ser Ser Gln Thr Pro Pro Pro Val Gly Arg Thr Ala
1               5                   10                  15

Ala His Gly Gly Arg His Lys His Asp Asp Asp Pro Ser Thr Pro
                20                  25                  30

Arg Gly Phe Cys Ala Lys Tyr Phe Ser Arg Glu Ser Cys Leu Leu Leu
            35                  40                  45

Ala Leu Val Thr Val Leu Leu Val Leu Pro Leu Val Leu Pro Pro
50                      55                  60

Leu Pro Ala Pro Pro Leu Ala Leu Leu Leu Val Pro Val Ala Met Leu
65                  70                  75                  80

Ala Val Leu Leu Val Leu Ala Leu Met Pro Ala Ala Gly Gly Arg
                85                  90                  95

Asn Glu Ala Val Asp Pro Ala Ser Tyr Leu
            100                 105

<210> SEQ ID NO 11
<211> LENGTH: 118
<212> TYPE: PRT
<213> ORGANISM: Zea mays

<400> SEQUENCE: 11

Met Met Leu His Cys Thr Phe Ala Ile Ser Glu Ala Pro Ala Arg Ala
1               5                   10                  15

Leu Ala Leu Gly Gln Val Ser Val Met Arg Ala Met Pro Gln Glu Glu
                20                  25                  30

Glu Ala Ala Val Ala Thr Thr Thr Met Ala Gly Gly Lys Val Ala Ala
            35                  40                  45

Leu Leu Ala Thr Ala Ala Ala Leu Leu Leu Leu Pro Leu Ala Leu
50                  55                  60

Pro Pro Leu Pro Pro Pro Thr Gln Leu Leu Phe Val Pro Val Val
65                  70                  75                  80

Leu Leu Leu Leu Val Ala Ser Leu Ala Phe Cys Pro Ala Ala Thr Ser
                85                  90                  95

Ser Pro Ser Pro Met His Ala Ala Asp His Gly Ser Phe Gly Thr Thr
            100                 105                 110

Gly Ser Pro His Leu Cys
        115

<210> SEQ ID NO 12
<211> LENGTH: 126
<212> TYPE: PRT
<213> ORGANISM: Zea mays

<400> SEQUENCE: 12

Met Pro Val Ala Ser Ser Leu Met Ala Met Glu Leu Glu Thr Asp Gln
1               5                   10                  15

Leu Ala Trp Ala Glu Gln Gln Arg Gln Gln Asn Arg Arg Gln Thr Met
            20                  25                  30

Val Val Cys Arg Lys Ser Asp Ala Ala Val Ala Lys Gly Gln Gln Arg
        35                  40                  45

Gln Asn Ala Ser Pro Pro Ser Pro Lys Pro Pro Ala Gly Gly Leu
    50                  55                  60

Ser Ala Glu Ala Phe Leu Val Leu Ala Cys Val Ala Val Ser Leu Ile
65                  70                  75                  80

Val Leu Pro Leu Val Leu Pro Pro Leu Ser Pro Pro Pro Leu Leu
                85                  90                  95

Leu Leu Val Pro Val Cys Leu Leu Leu Leu Ala Ala Leu Ala Thr
                100                 105                 110

Phe Val Pro Ser Asp Val Arg Ser Met Pro Ser Ser Asn Leu
            115                 120                 125

<210> SEQ ID NO 13
<211> LENGTH: 103
<212> TYPE: PRT
<213> ORGANISM: Oryza sativa

<400> SEQUENCE: 13

Met Lys Thr Thr Leu Ala Val Val Glu Gly Thr Arg Ala His Ile Val
1               5                   10                  15

Asn Leu Ala Asn Ser Arg Ala Ser Arg Leu Asn Glu Arg Leu Ile Asp
            20                  25                  30

Pro Ala Ile Glu Ser Arg Ser Ile Ala Gly Ala Thr Pro Ala Pro Phe
        35                  40                  45

Glu Met Glu Thr Ala Met Val Leu Leu Leu Ala Leu Val Ala Phe
    50                  55                  60

Leu Leu Cys Tyr Pro Leu Val Leu Pro Pro Leu Pro Pro Ser Pro Pro
65                  70                  75                  80

Ala Leu Phe Ile Trp Ile Pro Val Phe Met Leu Leu Leu Phe Ala
                85                  90                  95

Leu Ala Leu Phe Pro Val Gln
            100

<210> SEQ ID NO 14
<211> LENGTH: 68
<212> TYPE: PRT
<213> ORGANISM: Oryza sativa

<400> SEQUENCE: 14

Met Val Met Leu Leu Ala Ala Ala Val Leu Leu Leu Leu Leu
1               5                   10                  15

Pro Leu Leu Leu Pro Pro Leu Pro Pro Pro Ser Leu Leu Leu Leu
            20                  25                  30

Val Pro Val Val Leu Leu Ala Leu Leu Ser Leu Ala Phe Leu Pro
        35                  40                  45

Asn Arg Asp Val Val Val Tyr Gly Gln Gln Pro Ala Ala Asp Gln Phe
    50                  55                  60

Phe Phe Arg Gln
65

<210> SEQ ID NO 15

```
<211> LENGTH: 147
<212> TYPE: PRT
<213> ORGANISM: Oryza sativa

<400> SEQUENCE: 15

Met Ser Phe Ala Ile Arg Ser Ser Glu Pro Glu Phe Trp Phe Leu Ile
1               5                   10                  15

Pro Ser Glu Glu Ala Ala Val Ala Val Ala Ala His Arg Leu Val Val
            20                  25                  30

Met Asp Gln Arg Arg Ser Gly Ser Ala Tyr Arg Pro Lys Arg Thr His
        35                  40                  45

Met Ala Ala Ala Glu Asp Glu His Arg Arg Pro Gly Thr Ser Ser Arg
    50                  55                  60

Arg Arg Val Ala Pro Thr Pro Thr Thr Gln Thr Gln Thr Gln Thr Ala
65                  70                  75                  80

Pro Gly Tyr Phe Thr Val Glu Leu Val Met Ala Phe Val Cys Val Thr
                85                  90                  95

Ala Ser Leu Val Leu Leu Pro Leu Val Leu Pro Pro Leu Pro Pro Pro
            100                 105                 110

Pro Ser Leu Leu Leu Val Val Pro Val Cys Leu Leu Ala Val Leu Val
        115                 120                 125

Ala Met Ala Phe Val Pro Leu Asp Ala Gln Ser Asn Val Val Gly Ser
    130                 135                 140

Ser Cys Leu
145

<210> SEQ ID NO 16
<211> LENGTH: 130
<212> TYPE: PRT
<213> ORGANISM: Oryza sativa

<400> SEQUENCE: 16

Met Glu Lys Gly Arg Gly Lys Ala Cys Gly Gly Gly Ser Thr Ala Pro
1               5                   10                  15

Pro Pro Pro Pro Ser Ser Ser Gly Lys Ser Gly Gly Gly Gly Gly Gly
            20                  25                  30

Ser Asn Ile Arg Glu Ala Ala Ala Ser Gly Gly Gly Gly Gly Val Trp
        35                  40                  45

Gly Lys Tyr Phe Ser Val Glu Ser Leu Leu Leu Leu Val Cys Val Thr
    50                  55                  60

Ala Ser Leu Val Ile Leu Pro Leu Val Leu Pro Pro Leu Pro Pro Pro
65                  70                  75                  80

Pro Ser Met Leu Met Leu Val Pro Val Ala Met Leu Val Leu Leu Leu
                85                  90                  95

Ala Leu Ala Phe Met Pro Thr Thr Thr Ser Ser Ser Ser Ser Ala Gly
            100                 105                 110

Gly Gly Gly Gly Gly Gly Arg Asn Gly Ala Thr Thr Gly His Ala Pro
        115                 120                 125

Tyr Leu
    130

<210> SEQ ID NO 17
<211> LENGTH: 127
<212> TYPE: PRT
<213> ORGANISM: Oryza sativa

<400> SEQUENCE: 17

Met Arg Gly Val Ile Leu Leu Arg Tyr Glu Glu Asp Ala Met Ala Gly
```

```
                1               5                  10                 15
His Arg Ser Thr Ala Ala Thr Gly Gly Arg Leu Tyr Gly Gln Val
                20                 25                 30

Gly Val Lys Arg Arg Val Val Glu Glu Thr Ala Ala Val Glu Val
                35                 40                 45

Gly Gly Gly Gly Gly Tyr Leu Gly Val Glu Ala Ala Val Leu Leu
                50                 55                 60

Gly Val Val Thr Ala Thr Leu Leu Val Leu Pro Leu Leu Pro Pro
65                  70                 75                 80

Leu Pro Pro Pro Pro Met Leu Leu Val Pro Val Ala Ile Phe
                85                 90                 95

Ala Val Leu Leu Leu Leu Val Leu Leu Pro Ser Asp Ala Lys Ser Ile
                100                105                110

Ala Ala Ala Gly Arg Pro Ser Ser Ser Ser Ser Ser Tyr Leu
                115                120                125

<210> SEQ ID NO 18
<211> LENGTH: 105
<212> TYPE: PRT
<213> ORGANISM: Zea mays

<400> SEQUENCE: 18

Met Gln Glu Glu Ala Ala Ser Ser Ser Ser Ser Ala Ser Pro Val
1               5                  10                 15

Met Asp Gly Gly Lys Ala Met Ala Val Leu Leu Ala Val Ala Ala
                20                 25                 30

Val Leu Leu Leu Leu Pro Leu Val Leu Pro Ser Leu Leu Leu Leu
                35                 40                 45

Pro Val Val Leu Leu Leu Val Val Ser Leu Ala Phe Phe Pro Ala
                50                 55                 60

Ala Gly Ser Asp Gly Val Val Ala Ala Ala Val Ala Gly Thr Tyr
65                  70                 75                 80

Gln Pro Pro Pro Pro Pro Ala Arg Ser Ser Pro Pro Ser Ser
                85                 90                 95

Ser Ser Ser Ser Ser Ser Arg Gln Leu
                100                105

<210> SEQ ID NO 19
<211> LENGTH: 105
<212> TYPE: PRT
<213> ORGANISM: Oryza sativa

<400> SEQUENCE: 19

Met Glu Gly Val Gly Ala Arg Gln Arg Arg Asn Pro Leu Ile Pro Arg
1               5                  10                 15

Pro Asn Gly Ser Lys Arg His Leu Gln His Gln His Gln Pro Asn Ala
                20                 25                 30

Ala Glu Lys Lys Thr Ala Ala Thr Ser Asn Tyr Phe Ser Ile Glu Ala
                35                 40                 45

Phe Leu Val Leu Val Phe Leu Thr Met Ser Leu Leu Ile Leu Pro Leu
                50                 55                 60

Val Leu Pro Pro Leu Pro Pro Pro Ser Leu Leu Leu Leu Leu Pro
65                  70                 75                 80

Val Cys Leu Leu Ile Leu Leu Val Val Leu Ala Phe Met Pro Thr Asp
                85                 90                 95

Val Arg Ser Met Ala Ser Ser Tyr Leu
                100                105
```

<210> SEQ ID NO 20
<211> LENGTH: 120
<212> TYPE: PRT
<213> ORGANISM: Oryza sativa

<400> SEQUENCE: 20

Met Glu Glu Gln Met Phe Arg Glu Gln Gln Met Gln Arg Gly Gly Arg
1               5                   10                  15

His His Gln His His Thr Thr Arg Glu Gln Glu Gln Gln Gln Lys Gln
                20                  25                  30

Gln Gln Arg Arg Arg Leu Met Asn Asn Ala Thr Asn Gly Gly Gly Gly
            35                  40                  45

Asp Gly Gly Ser Arg Cys Tyr Phe Ser Thr Glu Ala Ile Leu Val Leu
    50                  55                  60

Ala Cys Val Thr Val Ser Leu Leu Val Leu Pro Leu Ile Leu Pro Pro
65                  70                  75                  80

Leu Pro Pro Pro Thr Leu Leu Leu Leu Pro Val Cys Leu Leu
                85                  90                  95

Ala Leu Leu Val Val Leu Ala Phe Met Pro Thr Asp Met Arg Thr Met
            100                 105                 110

Ala Ser Ser Tyr Phe Phe Cys Leu
        115                 120

<210> SEQ ID NO 21
<211> LENGTH: 96
<212> TYPE: PRT
<213> ORGANISM: Glycine max

<400> SEQUENCE: 21

Met Met Met Val His Pro Arg Asp Gln Val Gly Gly Glu Thr His Lys
1               5                   10                  15

Asn Leu Val Glu Pro Asn Val Ala Ala Ser Lys Lys Ala Arg Asn Cys
                20                  25                  30

Ala Cys Met Val Ser Tyr Ser Val Leu Ile Leu Ala Leu Leu Thr Leu
            35                  40                  45

Ser Ile Leu Leu Leu Pro Leu Val Leu Pro Pro Leu Pro Pro Pro Pro
    50                  55                  60

Leu Leu Leu Leu Phe Val Pro Val Phe Ile Leu Val Val Leu Phe Phe
65                  70                  75                  80

Leu Ala Phe Ser Pro Ser Thr Leu Pro Asn Met Ala Val Leu Thr Ser
                85                  90                  95

<210> SEQ ID NO 22
<211> LENGTH: 96
<212> TYPE: PRT
<213> ORGANISM: Glycine max

<400> SEQUENCE: 22

Met Met Met Val His Pro Arg Asp Gln Val Gly Gly Asp Thr His Lys
1               5                   10                  15

Asn Leu Val Ala Pro Asn Val Ala Ala Ser Lys Lys Ala Arg Asn Cys
                20                  25                  30

Ala Cys Met Val Ser Tyr Ser Val Leu Ile Leu Ala Leu Leu Thr Leu
            35                  40                  45

Phe Ile Leu Leu Leu Pro Leu Val Leu Pro Pro Leu Pro Ala Pro Pro
    50                  55                  60

Leu Leu Leu Leu Phe Val Pro Val Phe Leu Leu Val Val Leu Phe Phe

```
                    65                  70                  75                  80
Leu Ala Phe Ser Pro Ser Thr Leu Pro Asn Met Ala Val Leu Thr Ser
                    85                  90                  95

<210> SEQ ID NO 23
<211> LENGTH: 66
<212> TYPE: PRT
<213> ORGANISM: Glycine max

<400> SEQUENCE: 23

Met Ala Arg Cys Phe Gly Leu Gly Ser Val Leu Val Leu Ala Ala Leu
1               5                   10                  15

Ala Ala Ser Met Val Val Leu Pro Leu Met Leu Pro Pro Leu Pro Pro
                20                  25                  30

Pro Pro Leu Val Leu Leu Phe Phe Pro Val Gly Ile Met Ala Ala Leu
            35                  40                  45

Met Leu Leu Ala Phe Ser Pro Ser Asp Gln Asn Gly Val Val Tyr Ala
50                  55                  60

Ser Thr
65

<210> SEQ ID NO 24
<211> LENGTH: 66
<212> TYPE: PRT
<213> ORGANISM: Glycine max

<400> SEQUENCE: 24

Met Ala Arg Cys Phe Gly Leu Gly Ser Val Leu Val Leu Ala Ala Leu
1               5                   10                  15

Ala Ala Ser Met Val Val Leu Pro Leu Met Leu Pro Pro Leu Pro Pro
                20                  25                  30

Pro Pro Leu Val Phe Phe Phe Pro Val Gly Ile Met Ala Ala Leu
            35                  40                  45

Met Leu Leu Val Phe Ser Pro Ser Asp Gln Asn Gly Val Val Tyr Ala
50                  55                  60

Thr Thr
65

<210> SEQ ID NO 25
<211> LENGTH: 90
<212> TYPE: PRT
<213> ORGANISM: Glycine max

<400> SEQUENCE: 25

Met Ser Ser Trp Leu Ile His Tyr Asn Lys Arg Phe Ile Ile Ser Ile
1               5                   10                  15

Ser Leu Ala Phe Met Leu Arg Leu Phe Gly Phe Lys Ser Thr Met Phe
                20                  25                  30

Met Val Val Leu Thr Ile Ala Ile Leu Val Leu Pro Leu Met Leu Pro
            35                  40                  45

Pro Leu Pro Pro Pro Met Ile Leu Met Leu Val Pro Leu Val Ile
50                  55                  60

Met Leu Leu Leu Val Lys Leu Ala Leu Tyr Ser Lys His Gly Pro Ala
65                  70                  75                  80

Asp Val Ile Tyr Gln Cys Asn Phe Thr Trp
                85                  90

<210> SEQ ID NO 26
<211> LENGTH: 130
```

<212> TYPE: PRT
<213> ORGANISM: Arabidopsis thaliana

<400> SEQUENCE: 26

Met Ile Arg Glu Ile Ser Asn Leu Gln Lys Asp Ile Asn Ile Gln
1               5                   10                  15

Asp Ser Tyr Ser Asn Asn Arg Val Met Asp Val Gly Arg Asn Asn Arg
            20                  25                  30

Lys Asn Met Ser Phe Arg Ser Pro Glu Lys Ser Lys Gln Glu Leu
        35                  40                  45

Arg Arg Ser Phe Ser Ala Gln Lys Arg Met Met Ile Pro Ala Asn Tyr
50                  55                  60

Phe Ser Leu Glu Ser Leu Phe Leu Leu Val Gly Leu Thr Ala Ser Leu
65                  70                  75                  80

Leu Ile Leu Pro Leu Val Leu Pro Pro Leu Pro Pro Pro Phe Met
            85                  90                  95

Leu Leu Leu Val Pro Ile Gly Ile Met Val Leu Leu Val Val Leu Ala
                100                 105                 110

Phe Met Pro Ser Ser His Ser Asn Ala Asn Thr Asp Val Thr Cys Asn
            115                 120                 125

Phe Met
    130

<210> SEQ ID NO 27
<211> LENGTH: 135
<212> TYPE: PRT
<213> ORGANISM: Arabidopsis thaliana

<400> SEQUENCE: 27

Met Ile Arg Glu Phe Ser Ser Leu Gln Asn Asp Ile Ile Asn Ile Gln
1               5                   10                  15

Glu His Tyr Ser Leu Asn Asn Asn Met Asp Val Arg Gly Asp His Asn
            20                  25                  30

Arg Lys Asn Thr Ser Phe Arg Gly Ser Ala Pro Ala Pro Ile Met Gly
        35                  40                  45

Lys Gln Glu Leu Phe Arg Thr Leu Ser Ser Gln Asn Ser Pro Arg Arg
50                  55                  60

Leu Ile Ser Ala Ser Tyr Phe Ser Leu Glu Ser Met Val Val Leu Val
65                  70                  75                  80

Gly Leu Thr Ala Ser Leu Leu Ile Leu Pro Leu Ile Leu Pro Pro Leu
            85                  90                  95

Pro Pro Pro Pro Phe Met Leu Leu Leu Ile Pro Ile Gly Ile Met Val
                100                 105                 110

Leu Leu Met Val Leu Ala Phe Met Pro Ser Ser Asn Ser Lys His Val
            115                 120                 125

Ser Ser Ser Ser Thr Phe Met
130                 135

<210> SEQ ID NO 28
<211> LENGTH: 88
<212> TYPE: PRT
<213> ORGANISM: Arabidopsis thaliana

<400> SEQUENCE: 28

Met Arg Val His Asp Gln Arg Leu Arg Phe Asp Val Thr Pro Lys Pro
1               5                   10                  15

Met Gly Leu Asn Gly Ser Ser Leu Ile Thr Ala Arg Ser Val Ala Leu
            20                  25                  30

```
Leu Leu Phe Leu Ser Leu Leu Leu Ile Leu Pro Pro Phe Leu Pro
            35                  40                  45
Pro Leu Pro Pro Pro Ala Thr Leu Leu Leu Pro Leu Leu Leu
 50                  55                  60
Met Ile Leu Leu Ile Phe Leu Ala Phe Ser Ser Asn Glu Pro Ser
 65                  70                  75                  80
Leu Ala Val Glu Pro Leu Asp Pro
                85
```

<210> SEQ ID NO 29
<211> LENGTH: 146
<212> TYPE: PRT
<213> ORGANISM: Sorghum bicolor

<400> SEQUENCE: 29

```
Met Ser Thr Gly Arg Pro Glu Asp Ile Gln Gln Leu Ile Asn Ser Ala
  1               5                  10                  15
Thr Ser Ser Pro Asn Arg Thr Ser Pro Ser Ala Ser Pro Ser Asp Met
                20                  25                  30
Glu Ser Gly Gly Gly Ser Ala Ser Pro Arg Ala Ser Thr Ser Asp
             35                  40                  45
Arg Arg Leu Gln Arg Ala Ala His Ser His Arg Glu Glu Trp Glu Pro
 50                  55                  60
Ala Ala Ala Ala Ser Gly Asp Gly Gly Thr Gly Ser Leu Trp Ser Arg
 65                  70                  75                  80
Tyr Phe Ser Leu Pro Val Leu Leu Leu Val Gly Val Thr Ala Ser Leu
                85                  90                  95
Val Ile Leu Pro Leu Val Leu Pro Pro Leu Pro Pro Pro Ser Met
            100                 105                 110
Leu Met Leu Val Pro Val Ala Met Leu Val Leu Leu Val Leu Ala
            115                 120                 125
Phe Met Pro Thr Ser Ser Val Arg Ala Gly Thr Gly Thr Gly Pro Thr
130                 135                 140
Tyr Met
145
```

<210> SEQ ID NO 30
<211> LENGTH: 88
<212> TYPE: PRT
<213> ORGANISM: Sorghum bicolor

<400> SEQUENCE: 30

```
Asn Ala Val Lys Arg His Leu Gln Gln Arg Gln Gln Glu Ala Asp Phe
  1               5                  10                  15
His Asp Lys Lys Val Ile Ala Ser Thr Tyr Phe Ser Ile Gly Ala Phe
                20                  25                  30
Leu Val Leu Ala Cys Leu Thr Phe Ser Leu Leu Ile Leu Pro Leu Val
             35                  40                  45
Leu Pro Pro Leu Pro Pro Pro Ser Leu Leu Leu Trp Leu Pro Val
 50                  55                  60
Cys Leu Leu Val Leu Leu Val Val Leu Ala Phe Met Pro Thr Asp Val
 65                  70                  75                  80
Arg Ser Met Ala Ser Ser Tyr Leu
                85
```

<210> SEQ ID NO 31
<211> LENGTH: 107

<212> TYPE: PRT
<213> ORGANISM: Sorghum bicolor

<400> SEQUENCE: 31

Met Ala Ser Arg Ser Ser Ala Leu Glu Gly Gly Ala Ala Ile Gln
1               5                   10                  15

Arg Arg Asn Asn Ala Val Lys Arg His Leu Gln Gln Arg Gln Gln Glu
            20                  25                  30

Ala Asp Phe His Asp Lys Lys Val Ile Ala Ser Thr Tyr Phe Ser Ile
        35                  40                  45

Gly Ala Phe Leu Val Leu Ala Cys Leu Thr Phe Ser Leu Leu Ile Leu
    50                  55                  60

Pro Leu Val Leu Pro Pro Leu Pro Pro Pro Ser Leu Leu Leu Trp
65                  70                  75                  80

Leu Pro Val Cys Leu Leu Val Leu Leu Val Leu Ala Phe Met Pro
                85                  90                  95

Thr Asp Val Arg Ser Val Ala Ala Ser Tyr Leu
                100                 105

<210> SEQ ID NO 32
<211> LENGTH: 58
<212> TYPE: PRT
<213> ORGANISM: Sorghum bicolor

<400> SEQUENCE: 32

Met Met Leu Leu Val Ala Thr Val Ile Leu Leu Cys Leu Pro Leu Val
1               5                   10                  15

Leu Pro Pro Leu Pro Pro Pro Leu Phe Leu Leu Phe Val Pro Val
            20                  25                  30

Val Met Met Leu Leu Leu Phe Ser Leu Val Leu Phe Pro Ser His His
        35                  40                  45

Cys Ala Cys Ser Ser Pro Thr Phe Thr Gln
    50                  55

<210> SEQ ID NO 33
<211> LENGTH: 148
<212> TYPE: PRT
<213> ORGANISM: Sorghum bicolor

<400> SEQUENCE: 33

Met Ser Phe Val Ala Gly Ser Ser Glu Ala Asp Gln Leu Trp Phe Leu
1               5                   10                  15

Ile Pro Ser Glu Gln Ala Arg Ala His Ala Val Gln Pro His His Pro
            20                  25                  30

Leu Ala Met Asp Arg Arg Ser Ser Ala Arg Arg Gly Asp Pro His
        35                  40                  45

Pro His Arg Arg Gly Ala Met His Gly Ala Ala Glu Gln Gln Lys Gln
    50                  55                  60

Gln Gln Gln Arg Gly Arg Pro Gln Gly Thr Arg Ala Ala Pro Pro Val
65                  70                  75                  80

Pro Pro Gly Tyr Phe Thr Ala Glu Leu Val Leu Ala Phe Leu Phe Val
                85                  90                  95

Ala Val Ser Leu Ala Phe Leu Pro Leu Val Leu Pro Pro Leu Ser Pro
                100                 105                 110

Pro Pro Phe Leu Leu Leu Leu Val Pro Val Gly Leu Leu Ala Val Leu
        115                 120                 125

Leu Ala Leu Ala Phe Val Pro Leu Asp Ala His Ser His Leu Val Val
    130                 135                 140

```
Gly Ser Ser Arg
145

<210> SEQ ID NO 34
<211> LENGTH: 120
<212> TYPE: PRT
<213> ORGANISM: Sorghum bicolor

<400> SEQUENCE: 34

Met Ala Glu Glu Arg Lys Gln Ala Gly Ser Arg Trp Pro Ala Gly Gly
1               5                   10                  15

Ser Gly Gly Gly Arg Met Arg Asp Ala Glu Gly Ser Gly Lys Met
            20                  25                  30

Arg Gly Arg Gln Ala Thr Lys Ala Arg Pro Val Val Leu Ala Pro Pro
        35                  40                  45

Gly Gln Gly Tyr Phe Thr Ala Gly Leu Ala Ala Leu Phe Leu Cys Leu
    50                  55                  60

Thr Ala Leu Leu Val Phe Leu Pro Leu Val Leu Pro Pro Leu Pro Pro
65                  70                  75                  80

Pro Pro Tyr Leu Leu Leu Val Pro Val Gly Leu Met Ala Val Leu
                85                  90                  95

Leu Ala Leu Val Ala Leu Val Pro Ser Asp Gly Arg Ala Ala Thr Ala
            100                 105                 110

Ala Val Ala Ser Ser Cys Val Cys
        115                 120

<210> SEQ ID NO 35
<211> LENGTH: 101
<212> TYPE: PRT
<213> ORGANISM: Sorghum bicolor

<400> SEQUENCE: 35

Met Arg Arg Ala Val Pro Gln Glu Glu Ala Val Ala Ala Ala Thr Thr
1               5                   10                  15

Thr Thr Met Asp Gly Gly Lys Val Val Ala Leu Leu Ala Thr Ala Ala
            20                  25                  30

Ala Leu Leu Leu Leu Leu Pro Leu Ala Leu Pro Pro Leu Pro Pro Pro
        35                  40                  45

Pro Thr Gln Leu Leu Phe Val Pro Val Val Met Leu Leu Leu Val Ala
    50                  55                  60

Ser Leu Ala Phe Cys Pro Thr Ala Ala Ser Ser Gly Gly Gly Gly Lys
65                  70                  75                  80

Ser Lys Leu Ala Asp Ala Asp His Gly Ser Ser Phe Arg Thr Thr Gly
                85                  90                  95

Ser Pro His Leu Arg
            100

<210> SEQ ID NO 36
<211> LENGTH: 106
<212> TYPE: PRT
<213> ORGANISM: Sorghum bicolor

<400> SEQUENCE: 36

Met Pro Ser Pro Ser Gln Thr Ser Pro Pro Val Gly Arg Arg Thr Ala
1               5                   10                  15

His Gly Gly Trp His Lys His Asp Asp Pro Ser Thr Pro Arg Gly Phe
            20                  25                  30

Cys Thr Lys Tyr Phe Ser Val Glu Ser Cys Leu Leu Leu Ala Leu Val
```

```
                    35                  40                  45
Ala Val Leu Leu Leu Val Leu Pro Leu Val Pro Pro Leu Pro Pro
 50                  55                  60

Pro Pro Leu Ala Val Leu Leu Val Pro Val Ala Met Leu Ala Val Leu
 65                  70                  75                  80

Leu Val Leu Ala Leu Met Pro Val Ala Ala Ala Ala Gly Ala Arg
                 85                  90                  95

Asn Glu Val Val Asp Pro Ala Ser Tyr Leu
            100                 105

<210> SEQ ID NO 37
<211> LENGTH: 72
<212> TYPE: PRT
<213> ORGANISM: Sorghum bicolor

<400> SEQUENCE: 37

Met Glu Arg Ser Met Val Thr Met Leu Leu Leu Ala Thr Ala Ala Val
 1               5                  10                  15

Val Leu Leu Leu Leu Pro Leu Leu Pro Ser Ser Leu Pro Pro Pro
                 20                  25                  30

Pro Ser Leu Leu Leu Val Val Pro Val Val Leu Leu Ser Leu Leu
             35                  40                  45

Ser Leu Ala Phe Leu Pro Thr Arg Asp Asp Asp Ala Ile Ala Ile
 50                  55                  60

Tyr Gly Ser Leu Arg Ser Val Gln
 65                  70

<210> SEQ ID NO 38
<211> LENGTH: 13
<212> TYPE: DNA
<213> ORGANISM: Artificial Sequence
<220> FEATURE:
<223> OTHER INFORMATION: primer

<400> SEQUENCE: 38
cgctagcccc aac                                                        13

<210> SEQ ID NO 39
<211> LENGTH: 27
<212> TYPE: DNA
<213> ORGANISM: Artificial Sequence
<220> FEATURE:
<223> OTHER INFORMATION: primer

<400> SEQUENCE: 39
cacataacac acaactttga tgcccac                                         27

<210> SEQ ID NO 40
<211> LENGTH: 459
<212> TYPE: DNA
<213> ORGANISM: Zea mays

<400> SEQUENCE: 40
atgtgccgcg gcctcccaac tccagctcca gctccagcgc ttcaatttca gtcccaggat     60
tgcagtcggc agcagcgagg tactacccaa gcaccgcccg gccgagcgag cgagtccgtg    120
cgtgcgtgca tggcagcaga gaggaaggcg cctcccgcc cggccgcctg cgggcgaatg     180
cgcggcgccg agggtgccaa gccgcggggc cgtcaggcaa aggcagcgcg ggcaccaccg    240
ggccaggggt acttcacggc ggggctggcg gcgctgttcc tttgcctcac cacgctgctc    300
gtgttcctgc ctctcgtgct gccgccgctg ccgccgccgc cgttgctgct gctgctcgtg    360
```

```
cccgtgggcc tcatggctgt actgcttgcg ctggcgctcg tgccgtccga cggccgggcc      420
gccgccgccg ccgtcgcttc ttcatcgtgc gtgtgctga                             459

<210> SEQ ID NO 41
<211> LENGTH: 360
<212> TYPE: DNA
<213> ORGANISM: Zea mays

<400> SEQUENCE: 41
atgcacctgc tcgacgacct ccgccaagac cgcggcggcg cggccgccca caccggcagc      60
cgcagtcgca agccgccccc gccccttgcc gccgccgcc ccgccgccgc ggggtcccg       120 gcgggctcct ccaccgccgc caccgccacc cacctgggcc cggaggcggc ggcgctgctg     180
gcgtgcgtca cggccacgct gctgctgctt ccgctggtcc tgccgcccct gccgccgccg     240
ccgccgctcc tcctcctcgt gcccgtcgcc atcttcgccg tcctgctact cctcgtgctc     300
ctcccctccg acgcccgcgc cgccgtcgcc acgcccacct cctccgcctc ctacttgtag     360

<210> SEQ ID NO 42
<211> LENGTH: 195
<212> TYPE: DNA
<213> ORGANISM: Zea mays

<400> SEQUENCE: 42
atgagcaaga gagtactgat gatgttgctg gcggcgacag tgatcctcct gtgcctgccg      60
ttggtgctgc cacccttcc gccaccaccg ctgtttcttc tcttcgtccc tgtggtgatg      120
atgctcctgc tcttctccct ggttttcttc ccgtctaacc actgtccatg ctcttctccg     180
accttcactc agtaa                                                      195

<210> SEQ ID NO 43
<211> LENGTH: 321
<212> TYPE: DNA
<213> ORGANISM: Zea mays

<400> SEQUENCE: 43
atgccgtcat cgtcgcagac accgccgccg ccggtcggga ggactgctgc tcacggcggc      60
cggcacaagc acgacgatga cgacccaagc acgccgaggg gcttctgcgc caagtacttc     120
tccagggagt cgtgcctcct gctcgccctc gtcaccgtgc tgctggtggt gctcccgctc     180
gtcctgccgc cgctcccggc gccgccgttg gcgctgctgc tcgtgccggt cgcaatgttg     240
gcggtgctgc tggtgctcgc gctcatgccg gcggcggcag gtggccggaa cgaggctgtg     300
gacccggcgt cgtacttgta g                                               321

<210> SEQ ID NO 44
<211> LENGTH: 357
<212> TYPE: DNA
<213> ORGANISM: Zea mays

<400> SEQUENCE: 44
atgatgctgc actgcacatt tgctatatct gaggctcctg cgcgcgcctt ggcccttggc      60
caggtgtctg tcatgcgggc gatgccgcag aagaagaag ccgcggtggc gacgacgacc      120
atggccgggg gcaaggtggc ggcgctgctg gccacgcgg ccgcgctgct gctgctgctc      180
ccgctggcgc tgccgccgct gccgccgccg cccacgcagc tgttgttcgt ccccgtggtc     240
ttgctgctcc tcgtgcgtc cctcgcgttc tgccccgccg cgacctcctc gccgtcgccg     300
atgcatgccg ccgaccacgg gtcgttcggg accactggat caccgcacct atgttga       357
```

<210> SEQ ID NO 45
<211> LENGTH: 381
<212> TYPE: DNA
<213> ORGANISM: Zea mays

<400> SEQUENCE: 45

```
atgccggttg cttcgtcgct aatggcgatg gagttggaga cggaccaact cgcctgggcg      60
gagcagcagc ggcagcagaa taggaggcag accatggtcg tctgcagaaa gagcgacgca     120
gcggtggcca aagggcagca gcgtcagaac gcttcgccgc cgtcgcccaa gcctccgccc     180
gcgggcgggc tcagcgcgga ggcgttcttg gttctggcgt gcgtcgccgt gtcgctcatc     240
gtgctgccgc tggtcctgcc gccgctgtcg ccccgccgc ctctgctgct gctggtgccg      300
gtgtgcctgc tcctgctcct cgccgcgctc gccaccttcg tgccgtcgga tgtcaggagc     360
atgccatcct ccaacttgta a                                                381
```

<210> SEQ ID NO 46
<211> LENGTH: 312
<212> TYPE: DNA
<213> ORGANISM: Oryza sativa

<400> SEQUENCE: 46

```
atgaagacga ctttggctgt ggtggaaggg accagggcac atattgttaa cctggcgaat      60
tcaagggcgt ctcgattgaa cgaacggctg atcgatccag caatcgagtc tcgatcgatt     120
gccggagcaa cacctgcgcc gtttgagatg gagacgcaa tggtgctgct gctgcttgca     180
ctggtcgcct tccttctctg ctaccctctt gttctaccac cgctgccgcc ttcgcccccg     240
gccctgttca tctggatacc ggtgttcatg ctgctcctgc tcttcgccct tgccctcttc     300
cctgttcagt aa                                                          312
```

<210> SEQ ID NO 47
<211> LENGTH: 207
<212> TYPE: DNA
<213> ORGANISM: Oryza sativa

<400> SEQUENCE: 47

```
atggtgatgc ttctcctcgc tgcggcggcg gtgctgctgc tgctgctccc gctgctgctc      60
ccgccgctgc cgccgccgcc gtcgctgctg ctgctcgtcc ccgtcgtgct gctgctggcg     120
ctcctttccc tcgctttcct ccccaaccgc gacgtcgtcg tctacggaca gcagccagct     180
gcggatcaat tcttcttccg acaatga                                          207
```

<210> SEQ ID NO 48
<211> LENGTH: 444
<212> TYPE: DNA
<213> ORGANISM: Oryza sativa

<400> SEQUENCE: 48

```
atgagctttg caatccgcag ctctgagcct gaattctggt tcttgatccc gtcggaagag      60
gcagcagtag cagtcgcagc acatcggctg gtggtgatgg atcagaggag aagcggatca     120
gcttatcgtc ctaagcggac acatatggcg gcggcggagg acgagcaccg gcggccgggg     180
acgtcgagcc gccgccgggt ggcgccgacg ccgacgacga agacgcagac gcagacggcg     240
cccggctact tcaccgtcga gctggtgatg gcgttcgtct gcgtgaccgc gtcgctcgtg     300
ctgctgccgc tcgtcctgcc gccgttgccg ccgccgccgt cgctgctgct ggtggtgccg     360
gtgtgcctgc tcgccgtcct ggtggccatg gcgttcgtcc cgctcgacgc gcagagcaac     420
```

```
gtcgtcggct cgtcttgctt gtag                                              444

<210> SEQ ID NO 49
<211> LENGTH: 537
<212> TYPE: DNA
<213> ORGANISM: Oryza sativa

<400> SEQUENCE: 49
atgtacttgt tgagcccaag aaatggcgac gaggaggacg aacaggagga atccaggag         60 ctgatcagcg acgacgagcc gcccaatctc aagttggcat cctgcgccac tgcagccagc       120
agcagcagca gcagcggcag cgacatggag aagggaagag gtaaagcctg cggcggcggg       180
agtacggcgc cgccgccgcc gccgccgtcg tcgtcaggta atccggcgg cggcggcggc        240 agcaatatca gggaggcggc ggctagcggc ggcggcggcg gcgtgtgggg caagtacttc       300
tcggtggagt cgctgctcct gctggtgtgc gtgacggcgt cgctggtgat cctcccgctc       360
gtgctgccgc cgctgccccc gccgccgtcg atgctgatgc tggtgccggt ggcgatgctg       420
gtgctgctgc tggcgctggc gttcatgccg acgacgacgt cgtcgtcgtc gtccgccggc       480
ggcggcggcg gcggcggccg caatggggcg acgacgggac atgctcccta cttgtag         537

<210> SEQ ID NO 50
<211> LENGTH: 384
<212> TYPE: DNA
<213> ORGANISM: Oryza sativa

<400> SEQUENCE: 50
atgcgaggag tcatcttgct gcgttacgag gaggacgcca tggccgggca caggtccacg        60
gcggcggcga cgggagggag attgtacgga caggtgggga tgaagcggag agtggtggag       120
gagacggcgg cggcggtgga agtaggcgga ggaggaggag ggtacttggg ggtggaggcg       180
gcggtgctgc tcggggtggt gacggcgacg ctgctggtgc tgccgctgct gctgccgccg       240
ctgccgccgc cgccgccgat gctgctgctc gtgcccgtcg ccatcttcgc cgtgctcctc       300
ctcctcgtcc tgctgccctc cgacgccaag tccatcgccg ccgctggccg accctcttct       360
tcctcctcct cctcctacct gtag                                              384

<210> SEQ ID NO 51
<211> LENGTH: 318
<212> TYPE: DNA
<213> ORGANISM: Oryza sativa

<400> SEQUENCE: 51
atgcaagaag aagcggcgtc gtcgtcgtcg tcgtcggcgt cgccggtgat ggacgggggc        60
aaggcgatgg cggtgctgct ggcggtggcg gccgcggtgc tgctgctgct cccgctcgtg       120
ctgccgtcgc tgctgctgct cctccccgtg gtgctgctcc tgctggtggt ttccctcgcc       180
ttcttccccg cggccggcag cgacggcgtc gtcgccgccg ccgcggtcgc cggcacctac       240
cagccgccgc cgcctccgcc tgctcggtcg tcaccgccgc cgtcgtcgtc gtcgtcatcg       300
tcgtcgcggc agctgtga                                                     318

<210> SEQ ID NO 52
<211> LENGTH: 318
<212> TYPE: DNA
<213> ORGANISM: Oryza sativa

<400> SEQUENCE: 52
atggaaggtg taggtgctag gcagaggagg aaccctctga tacccagacc aaacggttca        60
```

-continued

```
aagaggcatc tgcagcatca gcatcagcca aatgctgccg agaagaagac cgccgcgaca    120
tcgaattact tcagtatcga ggcgttcctc gtgctcgtct tcctcaccat gtcattgctc    180
atacttccat tggtgcttcc cccattgcct ccgccgccat cgctgctgct gctgctgcca    240
gtctgcctgc tcatcctgct ggttgtgctg gccttcatgc aacggatgt gcggagcatg     300 gcttcctctt acttgtaa                                                  318

<210> SEQ ID NO 53
<211> LENGTH: 363
<212> TYPE: DNA
<213> ORGANISM: Oryza sativa

<400> SEQUENCE: 53
atggaggaac agatgttcag agagcagcaa atgcagagag gtggaaggca tcatcagcat     60
cacaccacaa gggaacaaga acaacagcag aagcagcagc agcggcggcg gctgatgaac    120
aatgcgacca acggcggcgg cggcgacggc ggcagcaggg gctacttcag cacggaggcc    180
atcctggtgc tggcatgcgt caccgtgtcg ctgctggtgc tgccgctcat cctgccgccg    240
ctgccgccgc cgccgacgct gctgctgctg ctgccggtgt gcttgctggc gctcctggtg    300
gtgctggcct tcatgcccac tgacatgagg accatggcct cttcctactt tttttgtttg   360
tga                                                                  363

<210> SEQ ID NO 54
<211> LENGTH: 291
<212> TYPE: DNA
<213> ORGANISM: Glycine max

<400> SEQUENCE: 54
atgatgatgg tgcatcctcg tgatcaagta ggtggagaga cacacaagaa tttggtggag     60
ccaaacgtgg cagcttctaa gaaagctaga aattgtgcat gcatggtaag ttactcggtg    120
ttgattttgg ctcttctcac tttgtccatt tgttgctac ctttggtgtt acctcctctg     180
ccgccaccac ccttgttgct ctctctttgtt ccagttttca tcttggtggt tctctttttc   240
ttggcctttt caccctccac actacccaac atggctgttc ttacatcatg a             291

<210> SEQ ID NO 55
<211> LENGTH: 291
<212> TYPE: DNA
<213> ORGANISM: Glycine max

<400> SEQUENCE: 55
atgatgatgg tgcatcctcg tgatcaagta ggtggagaca cacacaagaa tttggtggcg     60
ccaaacgtgg cagcttctaa gaaagctaga aattgtgcat gcatggtaag ttattcggtg    120
ttgattttgg ctcttctgac tttgttcatt tgttgctgc ctttggtgtt gcctcctctg     180
ccggcaccac ccttgttgct ctctctttgtt cctgttttcc tcttggtggt tctctttttc   240
ttggcctttt caccttccac actacccaac atggctgttc ttacatcatg a             291

<210> SEQ ID NO 56
<211> LENGTH: 312
<212> TYPE: DNA
<213> ORGANISM: Glycine max

<400> SEQUENCE: 56
atggcgcgtt gttttggttt aggttccgtt ctggttctgg cggcgctcgc ggcgtcgatg     60
gtggttctgc cgctgatgct gccgccgctc ccgccgccgc cactagttct tctcttcttc    120
```

```
cccgtcggga tcatggcggc gctcatgttg ctcgcgttct cgccatcaga tcaaaacggc    180
gtcgtttacg cgtcgacgta gcgaaggtgg tgggaaaccg gatcagccgg tgccacattt    240
tggggtttct tgaaggttcc gatgggattg cttcgtttca tgtttttttt tttttttaag    300
ttacggtgtt aa                                                        312

<210> SEQ ID NO 57
<211> LENGTH: 201
<212> TYPE: DNA
<213> ORGANISM: Glycine max

<400> SEQUENCE: 57
atggcgcgtt gtttcggctt aggttccgtt ctggttctgg cggcgctcgc ggcgtcgatg     60
gtggtgctgc cgttgatgct cccgccgctc ccgccgccgc cgctggtttt tttttttttc    120
cccgtcggga tcatggcggc gctcatgttg cttgtgttct cgccgtcgga tcaaaacggc    180
gtcgtttacg ccaccacgta a                                              201

<210> SEQ ID NO 58
<211> LENGTH: 273
<212> TYPE: DNA
<213> ORGANISM: Glycine max

<400> SEQUENCE: 58
atgagctctt ggttgattca ctacaacaag agattcataa taagcatctc attagcgttt     60
atgctaaggc ttttttgggtt taaatcaacc atgttcatgg tggtgctgac catagcaatc   120
ttggttctac cactgatgct accacctcta cctccaccac caatgattct tatgttggtg    180
cctcttgtga taatgctgct tctggtgaaa ttggctttgt attccaaaca tggccctgca    240
gatgtcattt atcagtgtaa ttttacttgg tag                                 273

<210> SEQ ID NO 59
<211> LENGTH: 393
<212> TYPE: DNA
<213> ORGANISM: Arabidopsis thaliana

<400> SEQUENCE: 59
atgattcgag aaatctcaaa cttacaaaaa gatattataa acattcaaga cagttattcg     60
aacaaccgag tcatggacgt cggaagaaac aaccggaaaa catgagcttt cgaagttcg    120 ccggagaaaa gcaagcaaga gttacggcgg agtttctcgg cgcagaaaag gatgatgatc    180
ccggcgaatt atttcagttt agagtctctg ttcctattgg ttggtctaac ggcatctctg    240
ttaatacttc cgttagtttt gccgccgtta cctccgcctc cgtttatgct gctattggtt    300
cccattggga ttatggtttt actcgtcgtt cttgccttca tgccttcttc tcattctaat    360
gctaatacag atgtaacttg caatttcatg taa                                 393

<210> SEQ ID NO 60
<211> LENGTH: 408
<212> TYPE: DNA
<213> ORGANISM: Arabidopsis thaliana

<400> SEQUENCE: 60
atgattcgtg agttctccag tctacaaaac gacatcataa acattcaaga acattattct     60
ctcaacaaca acatggacgt gagaggagat cataaccgga aaaacacgag ttttcgtggt    120
tcagctccag ctccgattat ggggaagcaa gaattgtttc ggacattgtc gtcgcagaac    180
agtccaagga ggctaatatc agcgagttac ttcagtttag aatcaatggt tgtgcttgtt    240
```

```
ggtctcacag catctctctt gatcttaccg ttgattcttc caccattgcc tcctcctcct    300
tttatgctgc ttttgattcc tattgggatt atggttttgc ttatggttct tgctttcatg    360
ccttcttcta attccaaaca tgtttcttct tcttccactt ttatgtaa                 408
```

<210> SEQ ID NO 61  
<211> LENGTH: 267  
<212> TYPE: DNA  
<213> ORGANISM: Arabidopsis thaliana

<400> SEQUENCE: 61

```
atgagggttc atgatcaacg gctgagattt gatgtcacac ccaagccgat gggtttgaac    60
ggaagttctt tgatcacggc aagatccgtc gcacttcttc tctttctctc tctgcttctt    120
ctgattctgc caccgttcct gccgccgctt ccaccgcctc cggcgacact cctcctcctt    180
cctctactcc tcatgattct cctcattttc ttggcttttt ctccttctaa tgagcccagc    240
ctcgccgttg aacctctcga cccctga                                         267
```

<210> SEQ ID NO 62  
<211> LENGTH: 441  
<212> TYPE: DNA  
<213> ORGANISM: Sorghum bicolor

<400> SEQUENCE: 62

```
atgagcaccg gccggccgga ggacatccag cagctaatca acagtgccac tagtagcccc    60
aaccgcacta gtccatccgc ctcgcccagc gacatggaga gcggcggcgg aagcgcgtcc    120
tcgccgcgcg cttcgacgtc cgaccggcgc ctgcagaggg ccgcccacag tcacagggag    180
gagtgggagc tgctgctgc tgctagcgg gatggcggca cgggtagcct ctggtccagg      240
tacttctcgc tcccggtcct cctgctcgtc ggcgtcaccg cgtcgctggt gatcctcccg    300
ctcgtgctcc ccccgctacc gccgccgccg tcgatgctga tgctggtccc ggtggcaatg    360
ctggtcttgc tgctcgtgct ggcgttcatg ccgacgtcga gcgtccgcgc tgggacgggg    420
acggggccga cctacatgta g                                               441
```

<210> SEQ ID NO 63  
<211> LENGTH: 267  
<212> TYPE: DNA  
<213> ORGANISM: Sorghum bicolor

<400> SEQUENCE: 63

```
aatgccgtga agcggcacct gcagcagcgg cagcaggagg cggatttcca cgacaagaag    60
gtcatcgcgt ccacctactt cagcatcggc gcgttcctgg tgctcgcctg cctcaccttc    120
tcgctgctca tcctgcctct ggtgctgccg ccgctgccgc gccgccgtc gctgctgctg      180 tggctgccgg tctgcctgct cgtcctgctg gttgtgctgg ccttcatgcc gacagatgtg    240
cgcagcatgg cctcctctta cttgtaa                                         267
```

<210> SEQ ID NO 64  
<211> LENGTH: 324  
<212> TYPE: DNA  
<213> ORGANISM: Sorghum bicolor

<400> SEQUENCE: 64

```
atggcaagcc gatctagcgc gctggaagga ggggggcag caatacagcg gaggaataat      60
gccgtgaagc ggcacctgca gcagcggcag caggaggcga atttccacga caagaaggtc    120
atcgcgtcca cctacttcag catcggcgcg ttcctggtgc tcgcctgcct caccttctcg    180
```

```
ctgctcatcc tgccgctggt gctgccgccg ctgccgccgc cgccgtcgct gctgctgtgg      240
ctgccggtct gcctgctcgt cctgctggtt gtgctggcct tcatgccgac agatgtgcgc      300
agcgtggcgg cctcttactt gtaa                                             324
```

```
<210> SEQ ID NO 65
<211> LENGTH: 177
<212> TYPE: DNA
<213> ORGANISM: Sorghum bicolor

<400> SEQUENCE: 65
atgatgttgc tggtggcgac agtgatcctc ctgtgcctgc cattggtgct gccaccactt      60
ccgccaccac cgctgttcct tctcttcgtc cctgtggtga tgatgctcct gctcttctcc     120
ctggttctct ccccgtctca ccactgtgca tgctcttctc caaccttcac tcagtaa       177
```

```
<210> SEQ ID NO 66
<211> LENGTH: 447
<212> TYPE: DNA
<213> ORGANISM: Sorghum bicolor

<400> SEQUENCE: 66
atgagctttg tggccggcag ctctgaggct gatcaactct ggttcttgat cccgtcggaa      60
caagcacgag ctcacgcggt acagcctcat catccgttgg ccatggaccg gaggtcgtcg     120
gcgaggagga gaggcgatcc tcaccctcac cgccggggcg caatgcacgg tgccgccgag     180
cagcagaagc agcagcagca gcgcggccgg ccgcagggaa cgcgggcggc gccgcccgtg     240
ccgccgggct acttcacggc ggagctggtg ctggcgttcc tgttcgtggc cgtgtcgctg     300
gcgttcctcc cgctggtcct gccgccgctg tcgccgccgc cgttcctgct gctgctggtg     360
cccgtgggac tgctggccgt gctcctcgcg ctcgcgttcg tgccgctcga cgcgcacagc     420
cacctcgtcg tcggctcctc ccgctga                                         447
```

```
<210> SEQ ID NO 67
<211> LENGTH: 363
<212> TYPE: DNA
<213> ORGANISM: Sorghum bicolor

<400> SEQUENCE: 67
atggcggagg agaggaagca ggcgggctcc cgctggcccg ccggaggcag cggcggcggg      60
cgaatgcgcg acgccgaggg tggcagtggc aagatgcggg ccggcaggc aacaaaggca     120 aggcccgtag tactggcgcc gccgggccag gggtacttca cggcggggct ggcggcgctg     180
ttcctctgcc tcaccgcgct gctggtgttc ctgccgctcg tgctgccccc gctgccgccg     240
ccgccgtatc ttctgctgct cgtgccggtg ggcctcatgg ccgtactgct ggctctggtg     300
gcgctcgtgc cgtccgacgg ccgggccgcc accgccgccg tcgcgtcgtc gtgcgtgtgc     360
tga                                                                    363
```

```
<210> SEQ ID NO 68
<211> LENGTH: 306
<212> TYPE: DNA
<213> ORGANISM: Sorghum bicolor

<400> SEQUENCE: 68
atgcggcggg cggtgccgca ggaggaagcc gtggcggcgg cgacgacgac gaccatggac      60
gggggcaagg tggtggcgct gctggccacg gcggccgcgc tgctgctgct cctcccgctg     120
gcgctgcccc cgctgccgcc gccgccacg cagctgctgt tcgtccccgt cgtcatgctg     180
```

```
ctgctcgtgg cgtccctcgc cttctgcccc accgccgcga gcagcggcgg cggcggcaag    240
agcaagctcg ccgacgccga ccacgggtcg tcgtttcgga ctactggatc accgcacctg    300
cgctga                                                               306

<210> SEQ ID NO 69
<211> LENGTH: 321
<212> TYPE: DNA
<213> ORGANISM: Sorghum bicolor

<400> SEQUENCE: 69
atgccgtcgc cgtcgcagac atcgccgccg gtcgggaggc ggactgctca tggcggctgg     60
cacaagcacg atgacccaag cacgccgagg ggcttctgca ccaagtactt ctccgtggag    120
tcgtgcctcc tgctcgccct cgtcgccgtg ctgctgctgg tgctcccgct cgtcctgccg    180
ccgctcccgc cgccgccgtt ggcggtgctg ctcgtgccgg tcgcaatgtt ggcggtgctg    240
ctggtgctgg cgctcatgcc ggtggcggcg gcggcggcgg gtgcccggaa cgaggtcgtg    300
gacccggcgt cgtacttgta g                                              321

<210> SEQ ID NO 70
<211> LENGTH: 219
<212> TYPE: DNA
<213> ORGANISM: Sorghum bicolor

<400> SEQUENCE: 70
atggaacgaa gcatggtgac gatgctgctc ctcgcgacgg cggccgtggt gcttctgctg     60
ctcccgctgc tgctcccttc ttccctgccg ccaccgccgt cgctgctgct ggtcgtccct    120
gtcgtgctgc tgctctcgct gctttccctc gctttccttc ccacccgcga cgacgatgac    180
gctattgcta tctacggatc actccgatcc gtgcagtga                           219

<210> SEQ ID NO 71
<211> LENGTH: 2436
<212> TYPE: DNA
<213> ORGANISM: Zea mays

<400> SEQUENCE: 71
aacaattctt gctacatgac ataaaaataa taaatggtcg actgacttgt tacactgaca     60
gaaataacat ccaagtctcc caatccaatt ccccttaatg aagttagctt ttgttagcaa    120
ggcccatttt ctatgagcca cataaagaac ttgattttttg gtggttttttt ttctttacaa    180 atgtgtttaa aatgtaaacc ggtttcattt ctagtaaggt attgtataca gatttgacag    240
aaaatcttcc atttttccta gatttccaga taatgctttc tggactgtca ttaagatgga    300
acgacaccac ttgttcctaa atcttatccc acatatatat acttgaggtc atccactaat    360
aattagattt ttggcacact tactttcttc tggttacata attaataagg gcctgtttag    420
ataccaggag ctaaagaaaa agtggttaaa gtttagtcaa tttaggggt taaagatcta    480 aaccggaaga atgagtgact aaaataataa aagtgtaccc ttttagtcac ttttagctcc    540
taagaagaag ctaaccttta atcagtttgc ttttaacccc tggatccaaa caagtcctaa    600
atcaccggta taactaggca caatgcctca tcagacagcc aactgccaat cccaaattct    660
actttgttgt ccatttctaa ttttaatgcc tctgcctgca cgtatactat ttttgttttt    720
gattaagtca taccacatag gagaatcact caatttatta gtaattgtat tgtatgaact    780
gaatcatttg gcgtatattt ggctttcttt aagcacaggc acactgctac caaaagcatt    840
aggcgcttaa gcatcaccct tgtggctggc acgagaacca tttgattcac gacagattta    900
```

```
gcgcttgttt gaagtgttgg ctaaaactag caatctacag ggaagaacac catacattag    960
tactccgtcg ggacacgcca ccacatgccg ctgaaatata tccgcaacga ttctcccagc   1020
tgcttatagc tcagaagcaa gagccaaggc cggcagctaa ccacgactcg tctaatcatc   1080
cctggaccat agcgattaat aaattgatta agctagtaca tcgcccctag atttccggca   1140
gaattaagaa aaccgcgggc agcagagccg atgccgatgg caacaaagaa gaaggggctg   1200
ttggtactgc agccgcagtc tataaagata aaaattgtag aagtagtagg aagcttagcc   1260
ggagctggca tggcaggctg ctgctgagtg agcagcggtg ggggcctcct ggctggcgcg   1320
tggaaaaacc cgagcaaatg gcagcgtgaa gcacgtccga gactgaggtc aggcgtcggg   1380
cgggggttgc ggccagggga gacgaatgaa cccctgcccc cgcctggatc ccatcgcaaa   1440
agcccccctcc ccctctccgc cttcgcgcat attatattcg cgcaccatcg cagcaacttg   1500
cacgggcgcc gatgactagt tgcgccagat gcactgcatc tgctcggcgt ggtgcctcca   1560
acgtccaacc cctcttcctc ttgtctctcg tctacctctc ttctgcccct ctgcgtccgt   1620
gtctccatcg tcgtcgctgc gtgaggttga cgacgaccag tcacaggacc tgttcgttcc   1680
tcatgcgacc cagctagcta aaactggcat gcatggacat gctacgctgc tgcgtcaatc   1740
catctcacca ggtacgctgc tgtacatgct gctacgagcc tacgatcgat agcagtctgt   1800
gccttccttt gctcgatgcc gatgtttatc tgcatgtgat cgtattcgta tgcacggccc   1860
tccgccctct caagctgagt gcttttggt gggcccatcg tcctatatac gctcatcagt   1920
tcactgacga cgatataacg actgttgggg ttcagaaact acatattgtg gtgctcgccc   1980
gatctctttc ttgtatattc ttcttattat tagtctctct ctctctgaaa gaacaaggaa   2040
ctagatgtct tgttttgtgc ctcctactat acctttgcgt gtttttcttg cttttgtcca   2100
tggcttttca ccggtctgct gggtgaagta atttacacgc atgtcttacg cacgcgctcc   2160
ttcagttgtc cgcatatctg atcataacat cgcttcattc atgtgctgac gagatattt   2220
tcgccgccga gactgcagtg ctagctagct agatctggcc tgattcgccg atcgagcggt   2280
ggtgagacgg agtgcttcag ctcaaagact gctagtggta ggctggtagc tagctgtgtg   2340
cctgtgtgca gtgtgcactg ccactgcatg cgcggcgcct tggacttaag acggcagcac   2400
acgcacgcga ggaggcgtcg gctgaagcga gcgctc                             2436
```